United States Patent
Goff et al.

(10) Patent No.: US 10,314,989 B2
(45) Date of Patent: Jun. 11, 2019

(54) POSITION CONTROL DEVICES AND METHODS FOR USE WITH POSITIVE AIRWAY PRESSURE SYSTEMS

(71) Applicant: Hancock Medical, Inc., Mountain View, CA (US)

(72) Inventors: Thomas G. Goff, Mountain View, CA (US); Nathaniel L. Bowditch, Menlo Park, CA (US); Tarmigan Casebolt, San Francisco, CA (US)

(73) Assignee: Hancock Medical, Inc., Mountain View, CA (US)

(*) Notice: Subject to any disclaimer, the term of this patent is extended or adjusted under 35 U.S.C. 154(b) by 850 days.

(21) Appl. No.: 14/762,683

(22) PCT Filed: Jan. 28, 2014

(86) PCT No.: PCT/US2014/013440
§ 371 (c)(1),
(2) Date: Jul. 22, 2015

(87) PCT Pub. No.: WO2014/117179
PCT Pub. Date: Jul. 31, 2014

(65) Prior Publication Data
US 2015/0367092 A1 Dec. 24, 2015

Related U.S. Application Data

(60) Provisional application No. 61/757,632, filed on Jan. 28, 2013.

(51) Int. Cl.
*A61M 16/00* (2006.01)
*A61M 16/06* (2006.01)
(Continued)

(52) U.S. Cl.
CPC ....... *A61M 16/0003* (2014.02); *A61B 5/0875* (2013.01); *A61B 5/1126* (2013.01);
(Continued)

(58) Field of Classification Search
CPC .......... A61M 16/0866; A61M 16/0875; A61M 16/208; A61M 2230/62; A61M 16/00;
(Continued)

(56) References Cited

U.S. PATENT DOCUMENTS

| 3,649,964 A | 3/1972 | Schoelz et al. |
| 3,721,233 A | 3/1973 | Montgomery et al. |

(Continued)

FOREIGN PATENT DOCUMENTS

| CN | 101678220 A | 3/2010 |
| FR | 2853838 A1 | 10/2004 |

(Continued)

OTHER PUBLICATIONS

Goff et al.; U.S. Appl. No. 15/329,150 entitled "Portable pap device with humidification," filed Jan. 25, 2017.
(Continued)

*Primary Examiner* — Jan Christopher L Merene
*Assistant Examiner* — Joseph D. Boecker
(74) *Attorney, Agent, or Firm* — Shay Glenn LLP

(57) ABSTRACT

Described here are positive airway pressure (PAP) systems and methods with various mechanisms for altering the air pressure based in part on the head position of the user. This can be achieved actively or passively. Passively, pressure is altered when head position is altered, as gravity acts to open or close venting elements. Actively, head position information can then be communicated to a controller of the system which may be disposed within the housing having the position sensor or within a separate housing. The controller varies the output pressure of the pressure source, e.g. a
(Continued)

rotary compressor, based, at least in part, on the head position information provided.

20 Claims, 14 Drawing Sheets

(51) Int. Cl.
*A61M 16/08* (2006.01)
*A61M 16/20* (2006.01)
*A61B 5/087* (2006.01)
*A61B 5/11* (2006.01)
*A61B 5/00* (2006.01)

(52) U.S. Cl.
CPC .......... *A61B 5/4818* (2013.01); *A61B 5/4836* (2013.01); *A61B 5/6803* (2013.01); *A61M 16/0057* (2013.01); *A61M 16/0066* (2013.01); *A61M 16/06* (2013.01); *A61M 16/0683* (2013.01); *A61M 16/0875* (2013.01); *A61M 16/20* (2013.01); *A61B 2562/0204* (2013.01); *A61B 2562/0219* (2013.01); *A61B 2562/0247* (2013.01); *A61M 16/0063* (2014.02); *A61M 16/0069* (2014.02); *A61M 16/209* (2014.02); *A61M 2016/003* (2013.01); *A61M 2016/0027* (2013.01); *A61M 2016/0033* (2013.01); *A61M 2205/332* (2013.01); *A61M 2205/3306* (2013.01); *A61M 2205/3317* (2013.01); *A61M 2205/3334* (2013.01); *A61M 2205/3375* (2013.01); *A61M 2205/3569* (2013.01); *A61M 2205/3592* (2013.01); *A61M 2205/6045* (2013.01); *A61M 2205/8206* (2013.01); *A61M 2209/088* (2013.01); *A61M 2210/06* (2013.01); *A61M 2210/0662* (2013.01); *A61M 2230/62* (2013.01)

(58) Field of Classification Search
CPC .......... A61M 16/0003; A61M 16/0057; A61M 16/0063; A61M 16/0066; A61M 16/0069; A61M 16/022; A61M 16/06; A61M 16/08; A61M 16/209; A61M 2205/215; A61M 2205/3306; A61M 2205/3317; A61M 2205/332; A61M 2205/3334; A61B 5/0875; A61B 5/0876; A61B 5/087; A61B 5/4818; A61B 5/6803; G01N 11/10; G01N 11/105; G01N 11/12; G01N 11/14; G01F 1/54
See application file for complete search history.

(56) References Cited

U.S. PATENT DOCUMENTS

| | | | |
|---|---|---|---|
| 3,736,927 A | 6/1973 | Misaqi | |
| 3,822,698 A | 7/1974 | Guy | |
| 3,881,198 A | 5/1975 | Waters | |
| 3,998,213 A | 12/1976 | Price | |
| 4,019,508 A | 4/1977 | Der Estephanian et al. | |
| 4,037,595 A * | 7/1977 | Elam | A61M 16/208 128/205.11 |
| 4,206,644 A * | 6/1980 | Platt | A61B 5/08 128/204.23 |
| 4,233,972 A | 11/1980 | Hauff et al. | |
| 4,297,999 A | 11/1981 | Kitrell | |
| 4,381,267 A | 4/1983 | Jackson | |
| 4,430,995 A | 2/1984 | Hilton | |
| 4,549,542 A | 10/1985 | Chien | |
| 4,588,425 A | 5/1986 | Usry et al. | |
| 4,590,951 A | 5/1986 | O'Connor | |
| 4,644,947 A | 2/1987 | Whitwam et al. | |
| 4,765,316 A | 8/1988 | Marshall | |
| 4,782,832 A | 11/1988 | Trimble et al. | |
| 4,802,485 A | 2/1989 | Bowers et al. | |
| 4,829,998 A | 5/1989 | Jackson | |
| 4,836,219 A | 6/1989 | Hobson et al. | |
| 4,944,310 A | 7/1990 | Sullivan | |
| 5,035,239 A | 7/1991 | Edwards | |
| 5,046,492 A | 9/1991 | Stackhouse et al. | |
| 5,054,480 A | 10/1991 | Bare et al. | |
| 5,054,484 A | 10/1991 | Hebeler | |
| 5,104,430 A | 4/1992 | Her Mou | |
| 5,113,853 A | 5/1992 | Dickey | |
| 5,154,168 A | 10/1992 | Schlobohm | |
| 5,284,160 A | 2/1994 | Dryden | |
| 5,303,701 A | 4/1994 | Heins et al. | |
| 5,318,020 A | 6/1994 | Schegerin | |
| 5,349,946 A | 9/1994 | Mccomb | |
| 5,353,788 A | 10/1994 | Miles | |
| 5,372,130 A | 12/1994 | Stern et al. | |
| 5,394,870 A | 3/1995 | Johansson | |
| 5,461,934 A | 10/1995 | Budd | |
| 5,485,851 A | 1/1996 | Erickson | |
| 5,501,212 A | 3/1996 | Psaros | |
| 5,517,986 A | 5/1996 | Starr et al. | |
| 5,533,500 A | 7/1996 | Her Mou | |
| RE35,339 E | 10/1996 | Rapoport | |
| 5,564,124 A | 10/1996 | Elsherif et al. | |
| 5,577,496 A | 11/1996 | Blackwood et al. | |
| 5,649,533 A | 7/1997 | Oren | |
| 5,657,752 A | 8/1997 | Landis et al. | |
| 5,769,071 A | 6/1998 | Turnbull | |
| 5,928,189 A | 7/1999 | Phillips et al. | |
| 5,937,855 A | 8/1999 | Zdrojkowski et al. | |
| 5,950,621 A | 9/1999 | Klockseth et al. | |
| 5,954,050 A | 9/1999 | Christopher | |
| 5,961,447 A | 10/1999 | Raviv et al. | |
| D421,298 S | 2/2000 | Kenyon et al. | |
| 6,050,262 A | 4/2000 | Jay | |
| 6,122,773 A | 9/2000 | Katz | |
| 6,135,106 A | 10/2000 | Dirks et al. | |
| 6,179,586 B1 | 1/2001 | Herb et al. | |
| 6,213,119 B1 | 4/2001 | Brydon et al. | |
| 6,349,724 B1 | 2/2002 | Burton et al. | |
| 6,367,474 B1 | 4/2002 | Berthon Jones et al. | |
| 6,371,112 B1 | 4/2002 | Bibi | |
| 6,393,617 B1 | 5/2002 | Paris et al. | |
| 6,397,845 B1 | 6/2002 | Burton | |
| 6,431,171 B1 | 8/2002 | Burton | |
| 6,435,180 B1 | 8/2002 | Hewson et al. | |
| 6,435,184 B1 | 8/2002 | Ho | |
| 6,470,887 B1 | 10/2002 | Martinez | |
| 6,513,526 B2 | 2/2003 | Kwok et al. | |
| 6,532,960 B1 | 3/2003 | Yurko | |
| 6,561,190 B1 | 5/2003 | Kwok | |
| 6,561,191 B1 | 5/2003 | Kwok | |
| 6,615,831 B1 | 9/2003 | Tuitt et al. | |
| 6,622,311 B2 | 9/2003 | Diaz et al. | |
| 6,622,726 B1 | 9/2003 | Du | |
| 6,626,174 B1 * | 9/2003 | Genger | A61M 16/026 128/204.21 |
| 6,634,864 B1 | 10/2003 | Young et al. | |
| 6,694,978 B1 | 2/2004 | Bennarsten | |
| 6,705,314 B1 | 3/2004 | O'Dea | |
| 6,709,405 B2 | 3/2004 | Jonson | |
| 6,730,927 B1 * | 5/2004 | Smith | G01F 1/20 128/204.22 |
| 6,733,556 B1 | 5/2004 | Luigi | |
| 6,752,146 B1 | 6/2004 | Altshuler et al. | |
| 6,772,760 B2 | 8/2004 | Frater et al. | |
| 6,772,762 B2 | 8/2004 | Piesinger | |
| 6,793,629 B2 | 9/2004 | Rapoport et al. | |
| 6,854,465 B2 | 2/2005 | Bordewick et al. | |
| 6,881,192 B1 | 4/2005 | Park | |
| 6,889,691 B2 | 5/2005 | Eklund et al. | |
| 6,895,959 B2 | 5/2005 | Lukas | |
| 6,895,962 B2 | 5/2005 | Kullik et al. | |
| 6,918,389 B2 | 7/2005 | Seakins et al. | |
| 6,920,877 B2 | 7/2005 | Remmers et al. | |
| 6,932,084 B2 | 8/2005 | Estes et al. | |
| 6,973,929 B2 | 12/2005 | Gunaratnam | |

(56) References Cited

U.S. PATENT DOCUMENTS

| | | | |
|---|---|---|---|
| 6,990,980 B2 | 1/2006 | Richey | |
| 7,019,652 B2 | 3/2006 | Richardson | |
| 7,069,932 B2 | 7/2006 | Eaton et al. | |
| 7,086,422 B2 | 8/2006 | Huber et al. | |
| 7,089,941 B2 | 8/2006 | Bordewick et al. | |
| 7,096,864 B1 | 8/2006 | Mayer et al. | |
| 7,118,608 B2 | 10/2006 | Lovell | |
| 7,156,090 B2 | 1/2007 | Nomori | |
| 7,178,525 B2 | 2/2007 | Matula et al. | |
| 7,195,014 B2 | 3/2007 | Hoffman | |
| 7,200,873 B2 | 4/2007 | Klotz et al. | |
| 7,204,250 B1 | 4/2007 | Burton | |
| 7,255,103 B2 | 8/2007 | Bassin | |
| 7,297,119 B2 | 11/2007 | Westbrook et al. | |
| 7,357,136 B2 | 4/2008 | Ho et al. | |
| D570,473 S | 6/2008 | Hamaguchi et al. | |
| 7,382,247 B2 | 6/2008 | Welch et al. | |
| 7,406,966 B2 | 8/2008 | Wondka | |
| 7,406,996 B2 | 8/2008 | Schuh | |
| 7,471,290 B2 | 12/2008 | Wang et al. | |
| 7,478,635 B2 | 1/2009 | Wixey et al. | |
| 7,487,778 B2 | 2/2009 | Freitag | |
| 7,516,743 B2 | 4/2009 | Hoffman | |
| 7,575,005 B2 | 8/2009 | Mumford et al. | |
| 7,588,033 B2 | 9/2009 | Wondka | |
| 7,664,546 B2 | 2/2010 | Hartley et al. | |
| 7,681,575 B2 | 3/2010 | Wixey et al. | |
| 7,766,841 B2 | 8/2010 | Yamamoto et al. | |
| 7,887,492 B1 | 2/2011 | Rulkov et al. | |
| 7,913,692 B2 | 3/2011 | Kwok | |
| 7,934,500 B2 | 5/2011 | Madaus et al. | |
| 7,942,824 B1 | 5/2011 | Kayyali et al. | |
| 7,975,687 B2 | 7/2011 | Gründler et al. | |
| D643,929 S | 8/2011 | DelloStritto et al. | |
| 8,020,557 B2 | 9/2011 | Bordewick et al. | |
| 8,061,354 B2 | 11/2011 | Schneider et al. | |
| 8,069,852 B2 * | 12/2011 | Burton | A61B 5/04 |
| | | | 128/204.18 |
| D659,235 S | 5/2012 | Bertinetti et al. | |
| 8,172,766 B1 | 5/2012 | Kayyali et al. | |
| 8,316,848 B2 | 11/2012 | Kwok et al. | |
| 8,327,846 B2 | 12/2012 | Bowditch et al. | |
| 8,336,546 B2 | 12/2012 | Bowditch et al. | |
| 8,353,290 B2 | 1/2013 | Adams | |
| D683,444 S | 5/2013 | Inoue et al. | |
| D683,445 S | 5/2013 | Inoue | |
| 8,453,640 B2 | 6/2013 | Martin et al. | |
| 8,453,681 B2 | 6/2013 | Forrester et al. | |
| 8,475,370 B2 | 7/2013 | McCombie et al. | |
| 8,517,017 B2 | 8/2013 | Bowditch et al. | |
| D696,393 S | 12/2013 | Lu | |
| D696,394 S | 12/2013 | Lu | |
| 8,688,187 B2 | 4/2014 | DelloStritto et al. | |
| 8,720,439 B1 | 5/2014 | Kolkowski et al. | |
| 8,733,349 B2 | 5/2014 | Bath et al. | |
| 8,903,467 B2 | 12/2014 | Sweitzer et al. | |
| 8,919,344 B2 | 12/2014 | Bowditch et al. | |
| 8,925,546 B2 | 1/2015 | Bowditch et al. | |
| D732,158 S | 6/2015 | Salmon et al. | |
| D734,446 S | 7/2015 | Salmon et al. | |
| D740,929 S | 10/2015 | Pipe et al. | |
| D740,930 S | 10/2015 | Pipe et al. | |
| 9,216,264 B2 | 12/2015 | Ho | |
| 9,833,591 B1 * | 12/2017 | Ormrod | A61M 16/20 |
| 2002/0078958 A1 | 6/2002 | Stenzler | |
| 2002/0104541 A1 | 8/2002 | Bibi et al. | |
| 2003/0062045 A1 | 4/2003 | Woodring et al. | |
| 2003/0079749 A1 | 5/2003 | Strickland et al. | |
| 2004/0079373 A1 | 4/2004 | Mukaiyama et al. | |
| 2004/0163648 A1 | 8/2004 | Burton | |
| 2004/0186681 A1 | 9/2004 | Harle | |
| 2004/0226562 A1 | 11/2004 | Bordewick | |
| 2005/0005937 A1 | 1/2005 | Farrugia et al. | |
| 2005/0028811 A1 * | 2/2005 | Nelson | A61M 16/06 |
| | | | 128/200.11 |
| 2005/0034724 A1 | 2/2005 | O'Dea | |
| 2005/0068639 A1 | 3/2005 | Pierrat et al. | |
| 2005/0131288 A1 | 6/2005 | Turner et al. | |
| 2005/0133039 A1 | 6/2005 | Wood | |
| 2005/0188991 A1 | 9/2005 | Sun et al. | |
| 2006/0037613 A1 | 2/2006 | Kwok et al. | |
| 2006/0081250 A1 | 4/2006 | Bordewick et al. | |
| 2006/0096596 A1 | 5/2006 | Occhialini et al. | |
| 2006/0150973 A1 | 7/2006 | Chalvignac | |
| 2006/0150978 A1 | 7/2006 | Doshi et al. | |
| 2006/0180149 A1 | 8/2006 | Matarasso | |
| 2006/0231097 A1 | 10/2006 | Dougherty et al. | |
| 2006/0249149 A1 * | 11/2006 | Meier | A61B 5/087 |
| | | | 128/204.18 |
| 2007/0000493 A1 | 1/2007 | Cox | |
| 2007/0113854 A1 | 5/2007 | Mcauliffe | |
| 2007/0163592 A1 | 7/2007 | Reinstadtler et al. | |
| 2007/0169781 A1 | 7/2007 | Tang | |
| 2007/0208269 A1 | 9/2007 | Mumford et al. | |
| 2007/0221220 A1 | 9/2007 | Bright | |
| 2007/0240716 A1 | 10/2007 | Marx | |
| 2007/0247009 A1 | 10/2007 | Hoffman et al. | |
| 2007/0251527 A1 | 11/2007 | Sleeper | |
| 2007/0277825 A1 | 12/2007 | Bordewick et al. | |
| 2008/0006275 A1 | 1/2008 | Nickelson et al. | |
| 2008/0053451 A1 | 3/2008 | Bordewick et al. | |
| 2008/0060649 A1 | 3/2008 | Valise et al. | |
| 2008/0091090 A1 | 4/2008 | Guillory et al. | |
| 2008/0127976 A1 | 6/2008 | Acker et al. | |
| 2008/0178879 A1 | 7/2008 | Roberts et al. | |
| 2008/0185002 A1 | 8/2008 | Berthon-Jones et al. | |
| 2008/0202527 A1 | 8/2008 | Hutchinson et al. | |
| 2008/0216831 A1 | 9/2008 | McGinnis et al. | |
| 2008/0251079 A1 | 10/2008 | Richey | |
| 2008/0304986 A1 | 12/2008 | Kenyon et al. | |
| 2009/0044810 A1 | 2/2009 | Kwok et al. | |
| 2009/0065005 A1 | 3/2009 | Ades | |
| 2009/0078255 A1 | 3/2009 | Bowman et al. | |
| 2009/0078258 A1 | 3/2009 | Bowman et al. | |
| 2009/0078259 A1 | 3/2009 | Kooij et al. | |
| 2009/0194101 A1 | 8/2009 | Kenyon et al. | |
| 2010/0024811 A1 | 2/2010 | Henry et al. | |
| 2010/0083965 A1 | 4/2010 | Virr et al. | |
| 2010/0180895 A1 | 7/2010 | Kwok et al. | |
| 2010/0186745 A1 * | 7/2010 | Mashak | A61M 16/00 |
| | | | 128/204.26 |
| 2010/0191076 A1 | 7/2010 | Lewicke et al. | |
| 2010/0229867 A1 | 9/2010 | Bertinetti et al. | |
| 2010/0240982 A1 | 9/2010 | Westbrook et al. | |
| 2010/0312513 A1 | 12/2010 | Mayor et al. | |
| 2010/0319687 A1 | 12/2010 | Esaki et al. | |
| 2011/0046462 A1 | 2/2011 | Ono et al. | |
| 2011/0056489 A1 | 3/2011 | Slaker et al. | |
| 2011/0100366 A1 | 5/2011 | Chou | |
| 2011/0105915 A1 | 5/2011 | Bauer et al. | |
| 2011/0108031 A1 * | 5/2011 | Korneff | A61M 16/0875 |
| | | | 128/203.27 |
| 2011/0192400 A9 | 8/2011 | Burton et al. | |
| 2011/0295083 A1 | 12/2011 | Doelling et al. | |
| 2012/0097156 A1 | 4/2012 | Bowman et al. | |
| 2012/0146251 A1 | 6/2012 | Heine et al. | |
| 2012/0152239 A1 | 6/2012 | Shikani et al. | |
| 2012/0152255 A1 | 6/2012 | Barlow et al. | |
| 2012/0167879 A1 | 7/2012 | Bowman et al. | |
| 2012/0179005 A1 * | 7/2012 | McCool | A61B 5/0806 |
| | | | 600/301 |
| 2012/0266873 A1 | 10/2012 | Lalonde | |
| 2012/0298709 A1 | 11/2012 | Lalonde | |
| 2012/0304985 A1 | 12/2012 | Lalonde | |
| 2013/0060098 A1 | 3/2013 | Thomsen et al. | |
| 2013/0104883 A1 | 5/2013 | Lalonde | |
| 2013/0146054 A1 | 6/2013 | Ho | |
| 2013/0152936 A1 * | 6/2013 | Ho | A61M 16/06 |
| | | | 128/205.25 |
| 2013/0239966 A1 | 9/2013 | Klasek et al. | |
| 2013/0298908 A1 | 11/2013 | Tang et al. | |
| 2013/0306074 A1 | 11/2013 | Bowditch et al. | |
| 2013/0333701 A1 | 12/2013 | Herron | |
| 2014/0000600 A1 | 1/2014 | Dimatteo et al. | |

(56) References Cited

U.S. PATENT DOCUMENTS

| | | |
|---|---|---|
| 2014/0007881 A1 | 1/2014 | Rummery et al. |
| 2014/0053939 A1 | 2/2014 | Kaye et al. |
| 2014/0090649 A1 | 4/2014 | Groll et al. |
| 2014/0102456 A1 | 4/2014 | Ovizinsky et al. |
| 2014/0127996 A1 | 5/2014 | Park et al. |
| 2014/0144445 A1 | 5/2014 | Bowditch et al. |
| 2015/0040908 A1 | 2/2015 | Goff et al. |
| 2015/0083136 A1 | 3/2015 | Grashow et al. |
| 2015/0096565 A1 | 4/2015 | Bowditch et al. |
| 2015/0197378 A1 | 7/2015 | Miller et al. |
| 2016/0015916 A1 | 1/2016 | Goff et al. |

FOREIGN PATENT DOCUMENTS

| | | |
|---|---|---|
| WO | WO91/19527 A1 | 12/1991 |
| WO | WO99/13931 A1 | 3/1999 |
| WO | WO99/21602 A1 | 5/1999 |
| WO | WO02/085417 A2 | 10/2002 |
| WO | WO2007/149446 A2 | 12/2007 |
| WO | WO2008/028247 A1 | 3/2008 |
| WO | WO2010/107913 A2 | 9/2010 |
| WO | WO2011/127385 A1 | 10/2011 |

OTHER PUBLICATIONS

Loew et al.; Design U.S. Appl. No. 29/519,711 entitled "Positive airway pressure system console," filed Mar. 6, 2015.

Cartwright; Effect of sleep position on sleep apnea severity; SLEEP; 7(2); pp. 110-114; 1984 (year of pub. sufficiently earlier than effective US filing date and any foreign priority date).

Colrain et al.; The use of a nasal resistance valve to treat sleep disordered breathing (Abstract No. 0518); SLEEP 2008 22nd Ann. Mtg. Assoc. Prof. Sleep Soc., LLC; Baltimore, MD; vol. 31, Abstract Suppl.; p. A172; Jun. 7-12, 2008.

Gunaratnam et al.; U.S. Appl. No. 60/494,119 entitled "Nasal Assembly," filed Aug. 12, 2003 (119 pgs.).

Høfsoy et al.; Monitoring and therapy of sleep related breathing disorders; IEEE; 6th Ann. Workshop on Wearable Micro and Nano Technologies for Personalized Heath (pHealth); pp. 41-44; Jun. 24-26, 2009.

Kwok, Philip R.; U.S. Appl. No. 60/505,718 entitled "Ventilator mask and system," filed Sep. 25, 2003 (37 pgs.).

Massie et al.; Acceptance and adherence of a novel device in the treatment of mild to moderate obstructive sleep apnea (Abstract No. 0644); SLEEP 2008 22nd Ann. Mtg. Assoc. Prof. Sleep Soc., LLC; Baltimore, MD; vol. 31, Abstract Suppl.; p. A211; Jun. 7-12, 2008.

Oksenberg et al.; Association of body position with severity of apneic events in patients with severe non-positional obstructive sleep apnea; CHEST; 118(4); pp. 1018-1024; Oct. 2000.

Penzel et al.; Effect of sleep position and sleep stage on the collapsibility of the upper airways in patients with sleep apnea; SLEEP; 24(1); pp. 90-95; Feb. 2001.

Pevernagie et al.; Relations between sleep stage, posture and effective nasal CPAP levels in OSA; SLEEP; 15(2); pp. 162-167; 1992 (year of pub. sufficiently earlier than effective US filing date and any foreign priority date).

Rosenthal et al.; A novel expiratory pressure device to treat mild-moderate OSA (Abstract No. 0634); SLEEP 2008 22nd Ann. Mtg. Assoc. Prof. Sleep Soc., LLC; Baltimore, MD; vol. 31, Abstract Suppl.; p. A208; Jun. 7-12, 2008.

Goff et al.; U.S. Appl. No. 15/551,671 entitled "Hose for respiratory device," filed Aug. 17, 2017.

\* cited by examiner

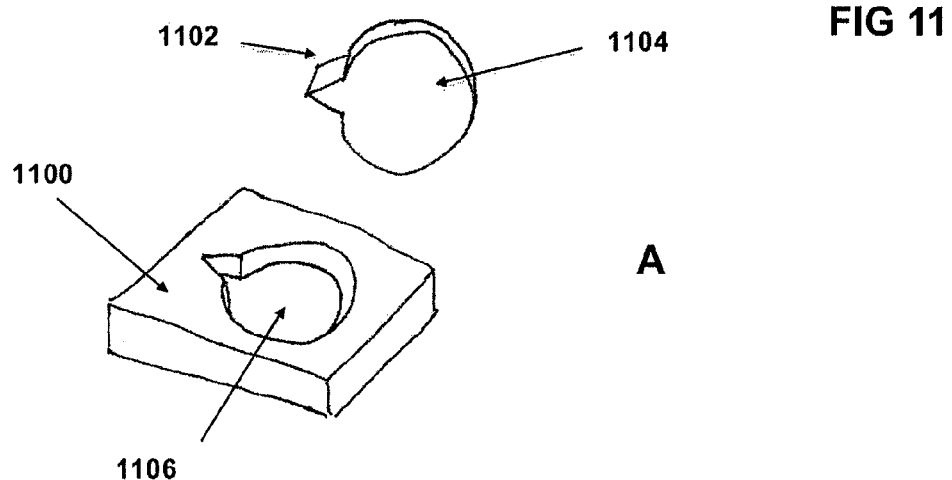
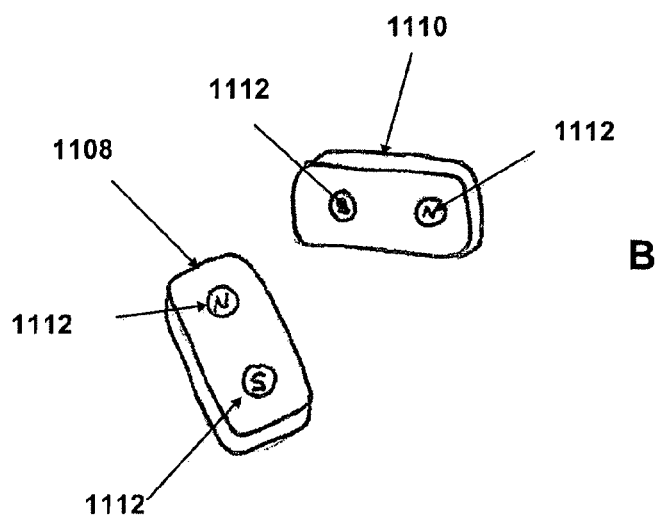
FIG 11

FIG. 15
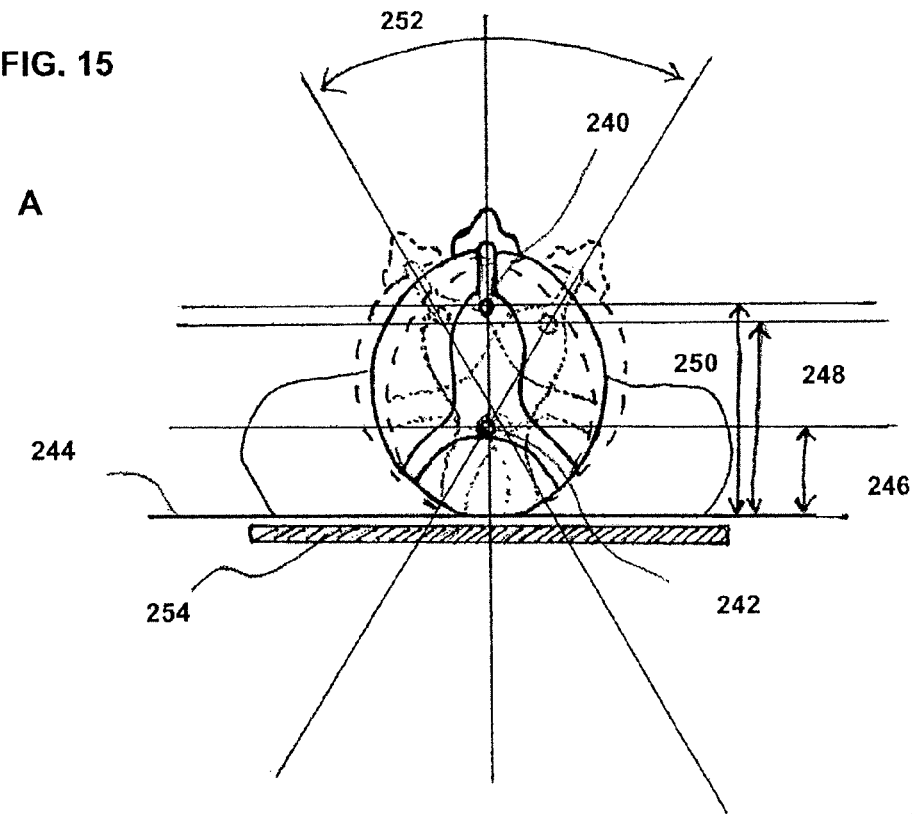
A
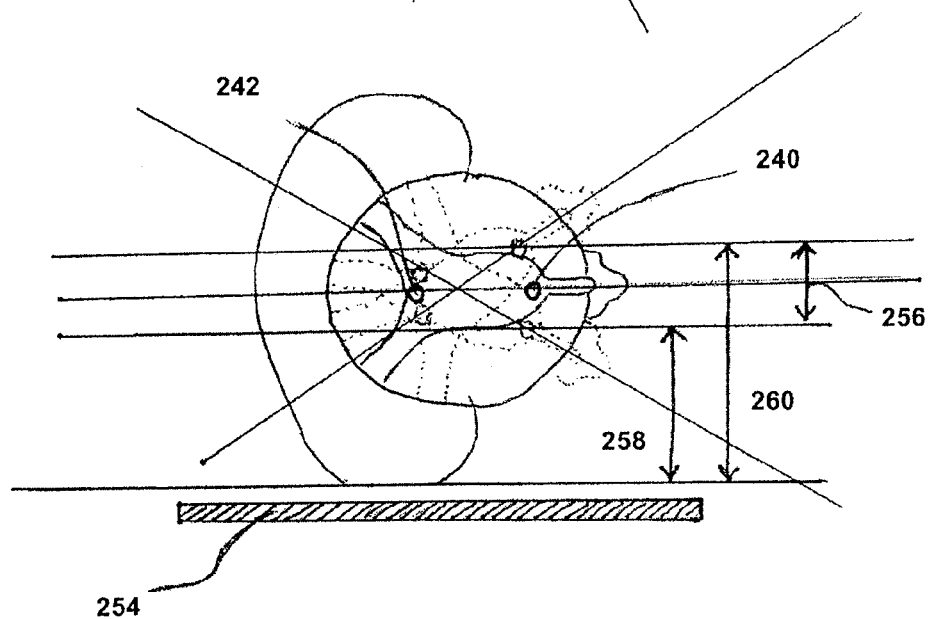
B

US 10,314,989 B2

POSITION CONTROL DEVICES AND METHODS FOR USE WITH POSITIVE AIRWAY PRESSURE SYSTEMS

CROSS REFERENCE TO RELATED APPLICATIONS

This application claims the benefit of and priority to U.S. Provisional Application Ser. No. 61/757,632, filed Jan. 28, 2013, the disclosure of which is hereby incorporated by reference in its entirety.

FIELD OF THE INVENTION

The invention is generally directed to position sensors and methods for controlling the treatment a patient receives, particularly to controlling a Positive Airway Pressure (PAP) device.

BACKGROUND OF THE INVENTION

During sleep, all muscles, including those of the upper airway, lose tone and relax. Obstructive Sleep Apnea (OSA) occurs when tissue blocks the upper airway during sleep. This will cause a drop in blood oxygen and a rise in blood carbon dioxide. The brain will sense these changes, and awaken the person enough to restore muscle tone to the structures of the upper airway, and the airway will reopen.

The severity of OSA is determined by the number of blockages per hour of sleep, also called the apnea-hypopnea index (AHI). These include complete blockages (apneas) and partial blockages (hypopneas). The severity of OSA, as determined by a sleep study, is classified as follows:

| SEVERITY | BLOCKAGES PER HOUR |
| --- | --- |
| Mild | 5-15 |
| Moderate | 15-30 |
| Severe | 30+ |

OSA disrupts restorative sleep. Chronic fatigue has long been recognized as the hallmark of OSA. But more recently, large clinical studies have shown a strong link between OSA and stroke and death. This link is independent of other risk factors for cardiovascular disease such as hypertension, obesity, high cholesterol, smoking and diabetes.

As discussed above, several structures can cause blockage of the upper airway: the tongue, the soft palate, the uvula, the lateral walls of the pharynx, the tonsils and the epiglottis. In most patients, the blockage is caused by a combination of these anatomical structures.

Many current procedures and devices have been used to stabilize, modify or remove tissue in the airway to treat OSA. In uvulopalatopharygoplasty (UPPP), the uvula, part of the soft palate and the tonsils are removed. A Repose stitch is used to tie the tongue to the mandible to prevent its posterior movement. Oral appliances move the mandible forward (very slightly) to create more space in the airway.

None of these approaches has achieved much more than a 50% success rate, with success defined as a 50% decrease in AHI to a score below 20. The limited success of these approaches likely stems from the fact that they don't address all anatomical sources of a blockage.

The most widely used therapeutic system for OSA is a PAP system such as a continuous positive airway pressure (CPAP) system. A CPAP system usually consists of three parts: a mask forming a largely airtight seal over the nose or nose and mouth, an air pressurizing housing or console and an elongated tube connecting the two. The mask contains one or more holes, usually at the junction with the tube. A CPAP system works by pressurizing the upper airway throughout the breathing cycle, essentially inflating the airway to keep it open. A CPAP system thus maintains a pneumatic splint throughout the respiratory cycle.

Unlike interventions that treat specific blockages, a CPAP system addresses all potential blockage sites. The success rate in patients (dropping AHI by >50%) exceeds 80%, and its cure rate (decreasing AHI below 5) is close to 50%. The drawback to a CPAP system is poor patient compliance, i.e. continuous use by the patient. In one large study, only 46% of patients were compliant with a CPAP system, even though compliance was defined as using the CPAP system at least 4 hours per night at least 5 nights per week.

Critical pressure is the airway pressure a given patient requires to maintain an open airway during sleep. Critical pressure is measured in cm of water, and will typically be between 6 and 14 cm of water for a patient requiring CPAP. In a given patient, the efficacy of a CPAP system goes up as pressure is increased. But, as higher pressure makes the CPAP system more uncomfortable to the patient, patient compliance drops. The goal of the healthcare professional in setting up a CPAP system for a patient is to achieve critical pressure without exceeding it. This will make the CPAP system both effective and tolerable.

In a given patient, there are several factors that affect critical pressure. The pressure supplied by the CPAP system necessary to achieve critical pressure varies through the breathing cycle. When a patient is exhaling, the patient is supplying some air pressure to the airway, and thus requires limited pressure from the CPAP system to maintain critical pressure. But when the patient is inhaling, he is decreasing pressure in the airway. During inhalation, more pressure is required by the CPAP system to maintain critical pressure in the airway. There are now many available CPAP systems that monitor the respiratory cycle, and provide less pressure during the portions of the respiratory cycle when less external pressure is required to maintain critical pressure in the airway. Such adaptive systems, which include systems commercially known as BiPAP and C-Flex, make CPAP systems more comfortable, improving the compliance of many patients. These adaptive systems have air pressure and air flow sensors integrated into the PAP console. These sensors measure air pressure and air flow in the conduit between the air compressor and the patient, and can thus track the respiratory cycle. So, during the respiratory cycle, critical pressure does not change. But the pressure contributed by the CPAP system to maintain critical pressure changes during the respiratory cycle.

Critical pressure can change based on sleeping position in many patients. Critical pressure will usually be higher when a patient is in a supine position (i.e. on his back) than when a patient is in a lateral position (on his side). This is because many of the structures that can block the airway, such as the tongue and uvula, are anterior to the airway. When a patient is in a supine position, gravity pulls these structures toward the airway, and a greater pressure (critical pressure) is required to keep the airway open. When a patient is in a lateral position, gravity is not pulling these structures directly into the airway, and thus less pressure is required to maintain an open airway. This was demonstrated in a study published in 2001 (Penzel T. et al. 2001. *Effect of Sleep Position and Sleep Stage on the Collapsibility of the Upper Airways in Patients with Sleep Apnea*; SLEEP 24(1):

90-95.). Additionally, most sleep studies used to diagnose OSA will track body position and will determine whether a patient has airway blockages more frequently when sleeping in a supine position. Other sleep studies have found that the lateral position results in fewer observed apneas than the supine position. (Cartwright R. et al. 1984 Effect of Sleep Position on Sleep Apnea Severity: SLEEP 7:110-114). (Pevernagie D. et al. 1992 Relations Between Sleep Stage, Posture, and Effective Nasal CPAP Levels in OSA: SLEEP 15: 162-167). Further studies have shown that apnea events in the supine position tend to be more severe, have longer duration, be accompanied by a greater oxygen desaturation and increased heart rate, and be more likely to result in arousals and awakenings. (Oksenberg A. et al. 2000 Association of Body Position with Severity of Apneic Events in Patients with Severe Non-positional Obstructive Sleep Apnea: CHEST 118: 1018-1024). Importantly, the air pressure and air flow sensors in bedside PAP consoles cannot currently determine a patient's sleeping position.

In furtherance of the inventions described in previous filings by the same inventors, herein we describe several means to gather and utilize sleeper position data with PAP systems to enhance treatment.

BRIEF SUMMARY

Described here are devices and methods for altering pressure in a positive airway pressure ("PAP") system for the treatment of patients with OSA or other breathing problems. The devices can sense head position, or otherwise alter the pressure based on head position. The sensors and sensing mechanisms could be used with a wearable PAP system, but are also intended for use with a standard bedside PAP system. The sensing elements broadly fall into three categories: gravity-driven physical sensing systems, secure attachment position sensing systems (which may include an accelerometer), and contact/pressure or proximity driven sensing systems. In addition to these active sensing technologies, passive technologies are disclosed which adjust the pressure by venting the excess pressure when in certain positions. These 'passive' systems may be driven by gravity.

The gravity-driven systems include one or more components that change a position or configuration due to gravity when the head position of the user changes. When the user alters their sleeping position, gravity alters the position or configuration of the gravity-driven component or components. These components, when altered, can then either affect a change to the system which lowers the pressure, such as opening venting valves, or create and send a signal to the PAP system to indicate that a change in pressure is desired, and the PAP system then adjusts the pressure.

In some embodiments, the gravity-driven physical sensing systems employ an element which, when actuated by gravity, modifies the airflow through the device, creating an airflow signature. This airflow signature is recognized by the air pressure and/or airflow sensors in the system (e.g., which may be integrated into a PAP system console), and used to determine the position of the device user.

In one preferred embodiment, the device includes a dangling element designed to hang into the airflow stream when the user is supine. The dangling element hangs into the airflow path and alters the airflow such that the PAP unit detects the alteration. This airflow alteration is the signal to the PAP unit to modify the pressure due to the change in user position. One way in which the dangling element is designed to alter the airflow is through oscillation within a known frequency range. The dangling element may comprise a weight element and a suspension material. By varying the weight, geometry, and suspension materials, different oscillation patterns can be achieved. For example, the geometry can be asymmetric to cause a greater force from the airflow to act on one side of the dangling element. In another embodiment, the shape of the dangling element can be altered to create oscillations. For example, the airpath around one side of the element could be longer than the airpath length around the other side. This would result in a lower local pressure on the side with the longer airpath, and would cause the dangling element to oscillate. By titrating the geometry, weight, and suspension material, the desired oscillation frequency can be achieved. These oscillations can be detected by the pressure and/or flow measurement sensors in the PAP unit. When these oscillations are detected, the system will know the user is in a supine position, and will adjust the PAP pressure accordingly. Most users will require a higher PAP pressure in the supine position than in other sleeping positions. When the user rolls to one side or the other, gravity pulls the dangling element to the side and far enough out of the airflow that the oscillations are changed. The change of position of the dangling element in the airflow removes or modifies the air signature. The machine recognizes this, and adjusts the PAP pressure accordingly. Most users will require a lower PAP pressure in non-supine positions. Alternatively, the dangling element or elements could work in the opposite fashion—creating the air signature when the user is in the non-supine position, and removing the air signature when the user is supine. This could be achieved by having a dangling element attached to each of the lateral sides of the airway. In the supine position, the dangling elements would fall substantially out of the airpath, but in either lateral position, one of the dangling elements would be pulled into the airpath to create the air signature The air signature can be created by a disruption in the airflow as it passes by the dangling element. The dangling element can have a geometry that disrupts the airflow in a predicted manner. The dangling element could also be caused to oscillate by the airstream. The airflow could displace the element momentarily, and then it could return to its position. This pattern could cycle many times, at a known frequency, which could be interpreted by the air pressure or airflow sensors located on the PAP machine. The oscillation information, together with any other information detected by the air flow and air pressure sensors, can be communicated to a controller which would control the output of the compressor based on programmed algorithms.

In another embodiment, the air signature could be created by passing the air through or past a structure that is designed to create sound (e.g., which may be at a frequency undetectable to the human ear). Several embodiments could achieve this selective sound signature based on position. For example, an element with a sound creating structure could be mounted within the airway such that it descends into the airpath by gravity in certain positions. For another example, a sound creating structure could be located at the edge of the airpath, or in a bypass airpath. A blocking element within this structure could selectively allow or block airflow according to gravity. This enables a first sound to be produced in a first position, and an addition position or positions which result in a change to that first sound that may include: eliminating the sound, increasing or decreasing its volume, or changing its frequency. Such frequencies could be below 20 Hz or above 60 kHz. This sound is sensed by the PAP device, and contains the position information about the sleeper, which is used to inform the appropriate pressure adjustment. The sound could be detected by one or more microphones in the PAP device, and communicated to the controller that controls the output of the compressor. The controller would utilize this and other information (such as air pressure and air flow information from the breathing cycle) to determine the compressor output based on programmed algorithms. The chosen frequency could also be undetectable to household pets such as dogs, cats, birds, or other household animals.

In another gravity-driven embodiment, a relief valve is provided in the air path system, and is actuated by gravity when certain sleeping positions are achieved. The valve passageway can have various sizes for pressure relief. For example, valves could be made to allow for one, two, three, four or more cm $H_2O$ of pressure relief when in the lateral position. Alternatively, the valves could be adjustable. A dial-adjustable valve, or other mechanism, could allow the user to change the rate of pressure relief through the valve passageway, thereby altering the amount of pressure adjustment. In one embodiment, a valve passageway or air exit path is open when the user is in the lateral position, but is closed when the user is supine. This maintains the higher pressure in the supine position, but lowers the pressure in the lateral position. This could be achieved through the use of a ball-in-track system, flapper valve(s), flutter valve(s) or other similar mechanisms. For example, in the supine position, the valve covers are held closed due to the force of gravity. In the lateral position, gravity acts to pull open one of the valve covers, allowing for the release of excess pressure. In another embodiment, in the supine position gravity pulls a ball within a track system to a low point where it blocks the valve exit port. In either lateral position, gravity acts on the ball to remove it from blocking the exit port, and the excess pressure is vented. With such a relief valve system, the PAP system would have to be programmed not to increase the PAP pressure output in response to a pressure drop which would occur when the patient is in a supine position.

In another gravity-driven embodiment, a mechanical gravity switch can be employed. An electrical circuit is incorporated with an open circuit that gets closed when gravity acts upon an element to bring it into contact with both ends of the open circuit. Such a system could be achieved using a ball in a track setup. When supine, gravity pulls the ball down the track to its lowest position, where it contacts both sides of the open circuit, thereby closing the circuit and signaling that the user is in the supine position. In other positions, gravity would keep the ball away from the ends of the circuit, leaving it in the open position. A hanging pendulum with a conductive element could produce the same results. In the desired position, say supine, the hanging element would contact both ends of the open circuit, thereby closing the circuit and indicating the user's sleeping position. Alternatively, an optical circuit could generate the signal. In one position, the optical circuit would sense the absence of a blocking element. In the alternate position, the blocking element would interrupt the optical circuit, thereby indicating a change in position. When the signal indicates the user is in the supine position, the PAP device administers the appropriate supine pressure. When the signal indicates the user is in the lateral position, the PAP device administers an appropriate lateral pressure (usually a reduced pressure).

A secure attachment position sensor is a sensor that can be removed and reattached to one or more portions of a PAP system. For instance, it could be removed from a PAP mask that is at the end of its service life and replaced onto a new PAP mask. The secure attachment position sensor provides position and orientation information about the user. The secure attachment position sensor attaches to a PAP mask, strap, hose, or structure on the user's head and/or body. The piece includes a sensor for determining the user's position. This information is relayed either wirelessly or through a small wire to the PAP system for use in appropriately titrating the PAP pressure. The sensor could be an accelerometer. Magnetometers, gyros, and other sensing elements known to the art could also be used alone or in combination to determine the sleeper's position and orientation. The sensor can have a secure attachment mechanism, which includes a predetermined, keyed, orientation for the sensor. This allows the sensor to be removed and reattached on the same or different devices. For example, when a user replaces a PAP mask, the sensor could be correctly oriented when attached to the new mask, due to the secure attachment system. A predetermined, keyed orientation for the sensor has the benefit of measuring the appropriate axis of motion, thus re-calibration would not be needed for such a replaced sensor. This would allow the sensor to be reusable or disposable. Further, the sensor attachment system could work with existing PAP accessories: masks, headstraps, scaffolds. It could also work with custom developed PAP accessories.

Several embodiments could enable the keyed function of the replaceable sensor. Geometry of mating parts is one way to key the elements. For example, a specific shape such as a triangle, diamond, etc. could be made on the sensor and a corresponding mating shape made on the mask or strap or headgear or part to which the sensor is to be attached. This would ensure that the two parts are attached together in a known, designated geometry. In some instances, it may be possible to attach the sensor in two ways, yielding the same sensing result. For example, if the sensor could be placed in one orientation as well as another orientation that is 180 degrees from the first orientation. Another embodiment could be realized using magnets. One or more magnets could be incorporated into the device to properly orient the sensor during reattachment. Keyed geometry could also be used in conjunction with other methods of fastening such as hook and loop systems, adhesives, elastomeric elements, or similar.

Another method to key the placement of the reattachable sensor is to key off of human anatomy. Structures such as the skull, ears, nose, nostrils, mouth and others could be used to place the sensor in a known location on the user's head. For example, a position sensor could be incorporated into a small ear bud or ear plug. This would allow the sensor to know repeatably and with certainty it's location on the head and orientation with respect to gravity. In addition, such an embodiment could incorporate noise dampening materials to further advantage.

Several advantages come out of having the sensor be removable and repeatably reattachable. This allows the mask to be cleaned and/or replaced periodically. This enables a more expensive sensing element to be used since it can be reusable. A reattachable sensor enables a retrofit for existing PAP systems and masks, enabling them to make use of position data for optimal PAP pressure administration.

Although a removable/reattachable sensor has many advantages, there may be circumstances under which a permanent, built-in sensor is desired. For example, as the costs of electronics continue to decline, a low-cost accelerometer could be permanently affixed to the user's headgear or mask during manufacturing. This sensor could be oriented as desired in manufacturing. It would allow easy setup, and could be connected via a wire or wirelessly as described herein. After its service life, the sensor would be discarded along with the element to which it is attached. In hospital applications or similar use environments where cross-contamination is a concern, the disposable element would help alleviate those concerns. This disposable solution has clear advantages for certain applications.

One choice for the position-sensing mechanism is an accelerometer (e.g., such as those described in U.S. Pat. Nos. 8,327,846 and 8,336,546). For such an embodiment, a power source and communication ability is required to enable the electronic sensor. The power source could be a small battery at or near the site of the sensor. This battery could be rechargeable or one-time use. Alternatively, the power source could be via a wire connecting to the PAP device, an off-body battery, or wall outlet source. Likewise, communication from the position sensor to the PAP device could be achieved either wired or wirelessly. If wired, it could be transmitted through conduit housed with the power transmission line. Or it could be transmitted via wire separately. Wirelessly, the information from the position sensor could be transmitted via Bluetooth, Low Energy Bluetooth, WiFi, or any other similar wireless means.

Multiple types of accelerometers could gather the necessary data for the position sensing application. Some possibilities are: 1-axis, 2-axis, or 3-axis accelerometers or similar sensors. For a 1-axis sensor to gather the necessary 'supine' or 'lateral' position data, it would need to be locked down in the other two axes during manufacturing, assembly, or setup. The other two axes would need to be oriented and defined such that the one axis of measurement is indicating the rotation of interest from supine to lateral. The other two axes need to be permanently defined in manufacturing; this could be achieved via fittings, adhesives, geometry or similar method. For instance, the 1-axis accelerometer would need to be oriented on the device such that it's axis of measurement aligns with that of the user's head rotating from supine to lateral and back. There may be specific advantages of a 1-axis accelerometer, such as cost and simplicity of code, which may reduce power needs. As such, it becomes very important to properly orient such a sensor to get useful readings. Such a system could be calibrated during manufacturing or assembly, removing the calibration step from the user.

Another possibility is a 2-axis sensor. For a 2-axis sensor such as an accelerometer, 1 of the axes would need to be locked down during manufacturing. Information gathered from the other 2 axes could be used to determine supine and lateral positions. Such a system could be calibrated during manufacturing or assembly, removing the calibration step from the user.

Another possibility is a 3-axis sensor. A 3-axis position sensor, such as an accelerometer, would not need any axes to be specially aligned. It would require a calibration step to define a known orientation once to enable it to determine lateral and supine positions.

Another embodiment to sense the position of the sleeper is to utilize pressure and/or contact sensors. These pressure and/or contact sensors could be placed on the sides of the device, or any other sleep surface contacting device surface. For example, a pressure sensor placed on either side of the device would signal when the user is in the lateral position. A pressure and/or contact sensor placed on the system such that it contacts the pillow or sleeping surface when the user is supine would indicate the supine sleeping orientation. Data from the pressure/contact sensors could then be used to adjust the PAP pressure to a therapeutically appropriate level. Such pressure/contact sensors could be placed on a wearable PAP device, headstraps, masks, tubing, scaffolding, ears, or any other worn element.

In another embodiment, proximity sensors are used to determine head position. For example, a small transmitter could be placed on either side of the head, and a receiver within or under the user's pillow. When in the lateral sleeping position, one of the transmitters would be closer to the receiver and one would be farther, allowing the system to determine the sleeping position. In the supine position, the two transmitters are located on the sides of the head such that they are roughly equidistant from the receiver. In the supine position, the two transmitters would also be at a distant between the closest transmitter and the furthest transmitter in the lateral position, assuming a roughly equivalent pillow height in each case. In such a way the sleeper's position could be determined. Of course, sleeping position could be determined by using proximity sensors in other ways as well. One such way would be to place the transmitters on the front and back of the head, and measure in the manner described above. Another way to determine the position using proximity sensors would be to place a sensor on each side of the head, and a sensing layer inside the sleeper's pillow. When the head sensor and pillow sensor are in close proximity, the user is in the lateral position.

Transmission of data gathered by the position/orientation sensing elements can be transmitted wirelessly to a control unit (via Bluetooth or other protocol), or can be transmitted via wire to the control unit. Batteries at or near the sensor placement can provide power for the above-described devices. Alternatively, power can be provided via a wired connection to a battery or power source. To reduce power demands, low-power sensing solutions and transmission protocols can be utilized. For example, low-power Bluetooth combined with reduced, optimized data transmission rates could reduce power requirements and enhance battery life.

Any of the above-described position sensing embodiments can be mounted to either directly to the patient, or to headgear, masks, straps, scaffolding, tubing, or wearable PAP systems. The position sensing elements may be manufactured such that they are reusable or disposable. The position sensing elements may be used in conjunction with standard bedside PAP units, with wearable PAP units, or with any other PAP units or ventilation or respiratory equipment.

A system embodying features of the detachable position sensor has a head position sensor, such as an accelerometer, that is secured with a fixed orientation within or to a PAP mask, tubing, or on or to the harness assembly that is configured to secure to the user's head. The head position sensor is configured to sense the position/orientation of the patient's head with respect to a reference plane (e.g. a horizontal plane) and to generate a signal representing the sensed position of the patient's head. A suitable accelerometer is a Freescale 3-Axis MEMS Accelerometer (MMA845XQ), particularly the MMA8453Q model, which generates a signal series representing a three-axis orientation with respect to gravity.

Such a detachable electronic sensor would need the means to communicate with the controller of the PAP output. This could achieved either by a wire from the position sensor to the PAP system, or by wireless communication such as Bluetooth from the position sensor to the PAP controller. Such a controller would vary gas pressure source output by patient position as detected by the position sensor. The controller is configured to receive the head position signals and to determine a suitable pressure source output pressure for the particular sensed head position from the received head position signal. The controller preferably has a stored relationship between sensed head position and suitable pressure source output pressure and is configured to generate a control signal for the pressure source representing the determined suitable gas pressure. The control signal generated by the controller is transmitted to the pressure source, e.g. the driving motor of a compressor, to control the output of the pressure source so as to provide the determined suitable gas pressure for the sensed position of the patient's head.

In one embodiment, an air pressure sensor senses the actual gas pressure directed to or received by the user and the controller compares the directed or received sensed pressure with the desired or determined suitable pressure and adjusts the control signal to the pressure source so as to provide the pressure source output that provides the critical pressure that maintains patency in the patient's airway passage.

Alternatively, the pressure source may be operated at a constant pressure level and a control valve disposed between the pressure source and the patient's mask receives the control signal to control the output pressure. The control valve may be provided in the compressor outlet, in a gas flow line to the patient's mask or in the patient's mask, to provide the determined suitable gas pressure to the patient that maintains patency in the patient's airway passage.

Although the position-sensing system and the controller are described herein as two separate devices, they may be combined into a single device.

The controller is configured to determine suitable compressor output pressures from the head position signal-pressure source output pressure relationship for at least two patient head positions, one head position may be a supine position and another second patient position might be a lateral position, preferably at least 20° from the supine position. In one embodiment, the controller may be provided with a readable library listing a plurality of head position signals with corresponding suitable pressure source output pressures. In another embodiment, the controller has a preprogrammed algorithm representing a relationship between head position signal and corresponding suitable pressure source output pressure. The microprocessor is configured to use the received head position signals to calculate from the algorithm suitable pressure source output pressures and generate suitable control signals for the pressure source. The relationship between the head position signal and suitable pressure source output pressure may be a stepped function, e.g. two or more positions with suitable pressure source output pressure or a continuous function. There may be a gradual change in pressure between stepped functions. The continuous function preferably has a maximum rate of change in the pressure source output pressure with respect to head position with head positions between about 30° and 60° from the supine position (0°).

The set point for a suitable pressure source output pressure for one of the head positions, e.g. the supine position, may be set by a health professional based upon the patient's sleep study. The set point for other positions may also be set by the health professional.

In one embodiment, the supine position may be defined as within 30° of vertical, with vertical being the sleeping position where the nose is pointed directly upward, orthogonal to the sleeping plane which is horizontal.

Initially, a health professional may set the output pressure of the compressor for one or more of the patient's head positions that have been based upon a sleep study performed on the patient. The second head position may be at least 20° away from the first head position. Optionally, the health professional may also set the set point for the output pressure of the system when the patient's head is at other positions. Preferably, the controller is programmed to select a suitable compressor output pressure from a preset table or library for at least one head position or determine a suitable pressure from a preprogrammed algorithm that is based upon the sensed position of the patient's head. The algorithm defines the relationship between the head position signal and the suitable compressor output pressure.

In the gravity-driven embodiments described herein, the supine and lateral positions would be determined in manufacturing. In the sensor embodiments described herein, the position sensor may require calibration. With the position sensor mounted on the patient's head, mask, tubing or straps, the head position sensor is first calibrated, preferably when the patient's head is in a supine position. The calibrated head position sensor senses the patient's head position and generates a sensed head position signal that is transmitted to the controller. The controller determines a suitable pressure source output pressure for the sensed head position signal and generates a control signal for the pressure source to provide the suitable pressure output pressure. In one embodiment, the controller compares the determined suitable pressure source output pressure with the current pressure output of the pressure source and if they differ by a specified amount, the controller generates a new control signal for the pressure source. If they do not differ by the specified amount the system loops back and continues to monitor the patient's head position.

The pressure source output pressure requirements can vary between a low point at exhalation to a high point at inhalation for each position of the patient's head which forms an output pressure envelope for the patient.

During sleep, the position of the patient's head can be the most important determinant of critical pressure for the patient since the anatomical structures that might block the airway (such as the tongue, the soft palate, the uvula and the tonsils) are in the head. Thus, the position sensor that determines the position of the head can be valuable in effectively controlling the pressure output of a PAP system.

In one embodiment the PAP system provides a first (higher) gas pressure from the compressor when the patient's head is in a supine position and a second (lower) pressure when the patient's head is in a lateral position. The gas pressure supplied to the patient when the patient's head is in a lateral position would likely be 1-8 cm of water less than the pressure supplied when the patient's head is in the supine position. Additionally, the PAP system can vary pressure more continuously based on several patient sleeping positions. With such a system, higher pressure would be supplied to the patient by the pressure source the closer a person's head is to a completely supine position with the patient's nose oriented in a vertical plane. Slightly lower pressure could be supplied, for example, if a person's head was 20° off from the supine position and other positions further away from the supine position. The lowest gas pressure would usually be when the patient's head is in a lateral position 90° or more from the supine position.

The patient's head positions are described herein primarily in terms of the supine position, a lateral position and positions between these two positions about a longitudinal axis passing through the patient's head. The head position sensor may also sense when the patient's head is tilted toward or away from the patient's chest, or rotated further than a lateral position 90° away from the supine position. A patient whose head is tilted far forward during sleep (i.e. the chin is close to the chest), may experience an even higher frequency of airway blockages than when in a supine position and may need a higher gas pressure to maintain an open airway passage than when in a supine position.

The PAP system which modulates its output pressure based on a patient's head position while sleeping could also be used to determine whether a given patient's sleep apnea event frequency and severity are affected by sleeping position, and PAP system output could be modulated accordingly. For example, the PAP system pressure may be lowered from about 11 cm (of water) to about 9 cm as the patient moved from a supine to a lateral sleeping position. The system could also further modulate pressure output based upon whether the number of airway blockages increased or decreased (e.g. as measured by air pressure sensors in the PAP mask or within the gaseous flow from the compressor to the PAP mask) and the corresponding patient position.

The controller of the PAP system may be used to provide different pressure source output pressures within the pressure envelope at different points in the respiratory cycle at any given patient head positions. For example, higher pressure source output pressures may be provided during inhalation and lower pressure source output pressures during exhalation to maintain the critical pressure within the patient's airway passage.

The features of this invention would allow a PAP system to provide different suitable gas pressures depending on the head position of the patient. This would improve patient comfort while providing the critical pressure at different positions to maintain an open airway. Additionally, since patients prefer lower PAP pressures, such a system might also cause patients to prefer to sleep in positions (such as a lateral position) that cause the system to provide a lower gas pressure to the patient. The lower output pressure would also encourage the patient to sleep in a position that leads to fewer airway blockages. The lower output pressure would tend to disturb a person's sleep much less because of comfort of lower pressure and less noise due to the slower operation of the compressor drive motor.

The position sensors described herein can provide head position data to controllers that are part of either bedside PAP systems or wearable PAP systems.

These and other advantages of the invention will become more apparent from the following detailed description of embodiments of the invention when taken in conjunction with the accompanying exemplary drawings.

BRIEF DESCRIPTION OF DRAWINGS

FIG. 11A illustrates a way to key a sensor and base element to each other using unique geometry.

FIG. 11B illustrates a way to key a sensor and base element to each other using magnets.

FIGS. 15A and 15B show a variation of a system comprising proximity sensors.

DETAILED DESCRIPTION

Described here are devices and methods for altering pressure in a positive airway pressure (PAP) system for the treatment of patients with OSA or other breathing problems. Typically, the positive pressure systems described here may include a wearable mask for delivery of pressurized air to a user, a pressure source configured to provide the pressurized air, and an airway tube connecting the mask and the pressure source, which may define an airway between the pressure source and the user. In some instances, the pressure source may be at least partially housed in a bedside unit, whereas in other instances the pressure source may be part of a wearable system.

Figure 1:
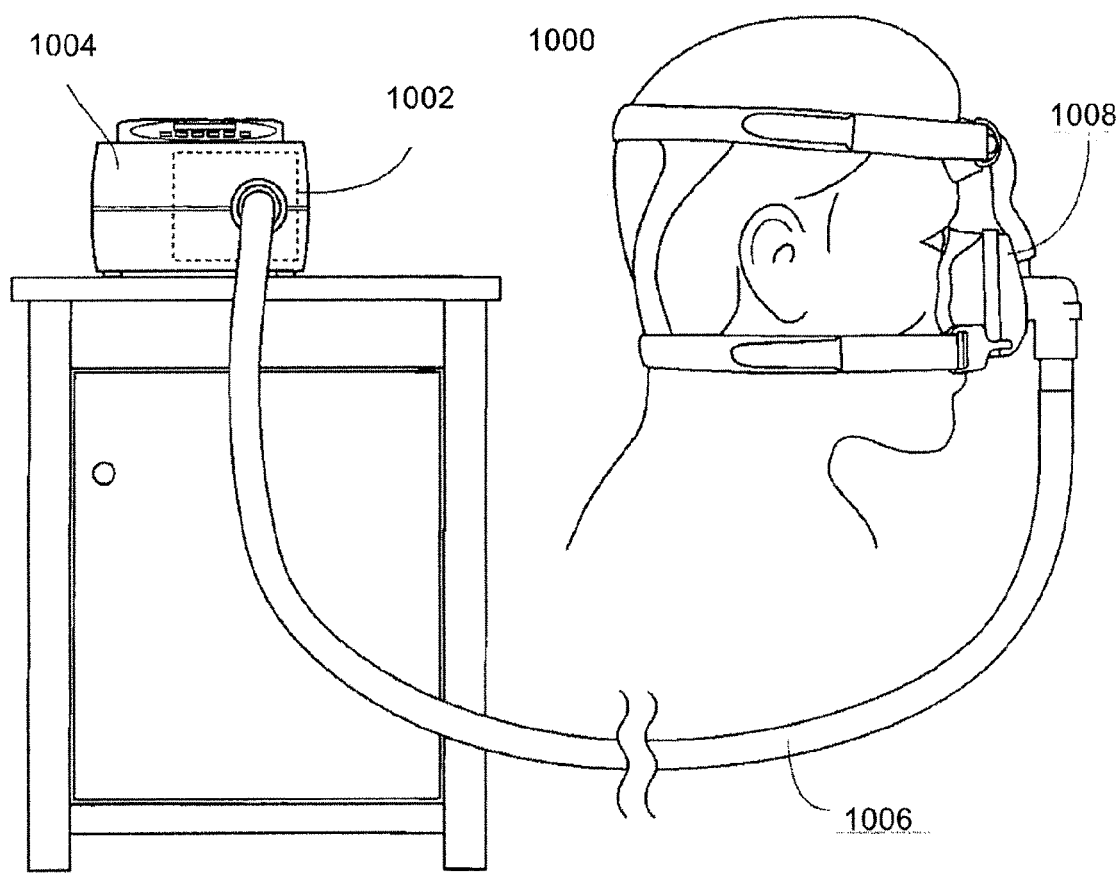
FIG. 1 depicts a bedside positive airway pressure system as described here.

FIG. 1 shows a variation of a bedside positive airway pressure system (1000) (e.g., a CPAP system). As shown there, the positive airway pressure system (1000) may include a pressure source (1002) (e.g., a compressor), which may be housed in a console (1004) that sits on the bedside table. The system may further comprise an airway tube (1006), which may connect the pressure source (1002) to a mask (1008) worn by the user. For example, a first end of the airway tube (1006) may be connected to the console (1004), and the airway tube (1006) may create an airway between the pressure source (1002) and the mask (1008). Typically, the airway tube (1006) includes a six foot CPAP tubing, although the airway tube (1006) may have any suitable length. The mask (1008), airway tube (1006) and console (1004) comprise the three primary elements of the system. Generally, the console (1004) may be reusable for several years, while the mask and tubing are intended to be disposed of every three months. It should be appreciated, however, that the components of the positive airway pressure system (1000) may be replaced at any suitable frequency. The masks of the systems described here may include any suitable elements, such as for example, a mask assembly including a mask, a headgear, and one or more straps.

Figure 2:
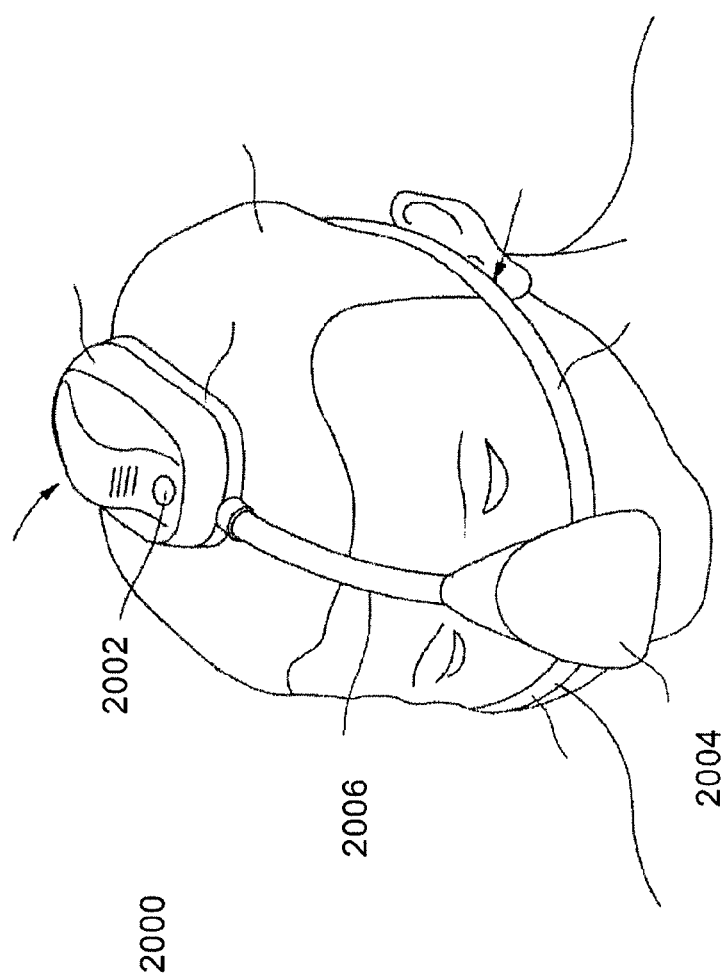
FIG. 2 depicts a wearable positive airway pressure system as described here.

FIG. 2 shows a wearable positive airway pressure system (2000) (e.g., a wearable CPAP system). As shown there, the positive airway pressure system (2000) may include a wearable housing (2002), a mask (2004), and an airway tube (2006) connecting the wearable housing (2002) to the mask (2004). Generally, the wearable housing (2002) includes a positive pressure source (e.g., a blower), and airway tube (2006) may create an airway between the pressure source and the mask. In some instances, the housing may be intended for reuse for several years, while the mask and tubing are intended to be replaced every three months, although it should be appreciated that the components of the positive airway pressure system (2000) may be replaced at any suitable frequency.

Figure 3:
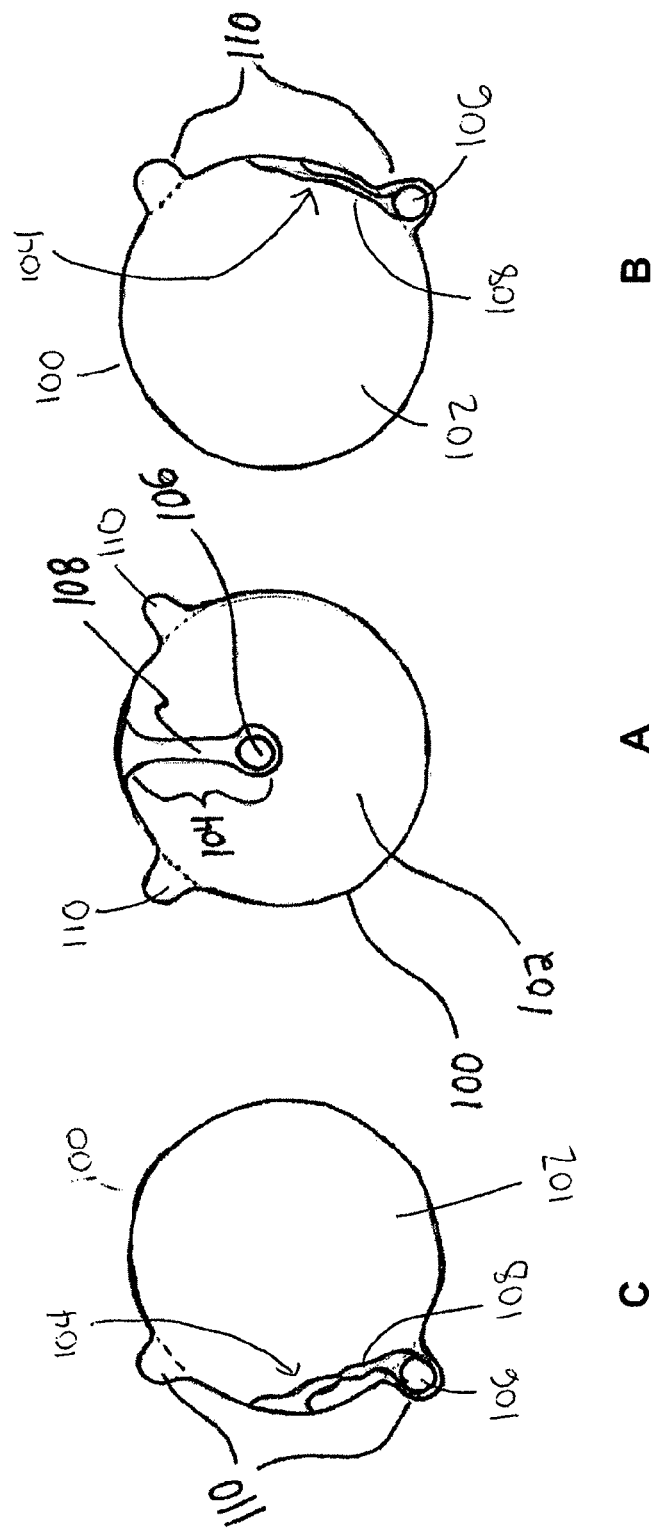
FIGS. 3A-3C show cross-sectional views of the airway tubing channel with a dangling element to create an air signature to indicate position.

The positive airway systems described above may be configured to sense a user's head position, and may be configured to alter pressure based on the sensed head position. For example, FIGS. 3A-3C show cross-sectional views of a section of an airway tube (100), which may be part of either a bedside or wearable positive airway pressure systems as discussed immediately above. Specifically, FIG. 3A shows a cross-sectional view of a segment of the airway tubing (100) having a channel (102) extending therethrough and a dangling element (104) positioned in the channel (102). As shown there, the dangling element (104) may comprise a weight element (106) and a suspension member (108) connecting the weight element (106) to a wall of the airway tubing (100). The position of the weight element (106) within the channel (102) may change depending on the orientation of a user's head position.

For example, in FIG. 3A, the dangling element (104) is shown hanging into the channel (102) due to gravity. In FIGS. 3A-3C, gravity is oriented down the page, from the top to bottom in these Figs. When acted upon by gravity, the dangling element (104) is pulled into the channel (102) to partially block the air path through the channel (102), thereby disrupting the airflow, and leaving an airflow signature that can be interpreted by the air pressure sensors in the PAP console. In some variations, the position of the dangling element (104) may correspond to the position of a user sleep in a supine position (i.e., on the user's back).

Shown here, the dangling element (104) includes a weight (106) suspended by a flexible suspension member (108). The weight (106) can be a body of any material of appropriate mass and density to produce the desired effects including but certainly not limited to: plastics, rubbers, metals, ceramics, paper, or the like. The suspension member (108) may be a tether, cord, or strip of any material of appropriate properties such as strength, weight and flexibility including but certainly not limited to: polymers, elastomers, fibers.

When the airway tubing (100) is rotated (e.g., in FIG. 3B, the cross-section is rotated 90 degrees clockwise, to represent the user sleeping on one side in the lateral position), gravity may pull the dangling element (104) out of the airpath through the channel (102). In some variations, the weight (106) may be pulled against an inner wall of the channel (102). In some variations, the airway tubing (100) may further comprise one or more recessed areas (110). In these variations, rotation of the airway tubing (100) may pull the weight (106) (and in some variations a portion of the suspension member (108)) at least partially into the recessed area (110), such that the weight (106) is housed at least partially out of the airpath of the channel (102). In some of these variations, the recessed area (110) may be sized such that the weight (106) is fully pulled into the recessed area (110), such that the weight (106) is housed entirely out of the airpath of the channel (102). Specifically, the suspension member (108) may deflect and the weight (106) may fall/be pulled into a recessed area (110) in the wall of the air channel, out of the airpath. In this position, the dangling element either does not produce an air signature, or produces an air signature different from that of the position shown in FIG. 3A.

In FIG. 3C, the cross-section is rotated 90 degrees counter-clockwise from FIG. 3A, to represent the user sleeping on the other side in the lateral position. In this position, gravity also pulls the dangling element (104) out of the airpath (102). In some instances, the weight (106) may be pulled at least partially or entirely into a recessed area (110), such as described in more detail above. In some variations, such as shown in FIGS. 3A-3C the airway tubing (100) may comprise two recessed areas. In these variations, the weight (106) may be pulled into a first recessed area (110) when the airway tubing (100) is rotated in a clockwise direction, and may be pulled into a second recessed area (110) when the airway tubing (100) is rotated in a clockwise direction.

While shown in FIGS. 3A-3C as being connected to airway tubing (100), the dangling element (104) may in other variations be connected to a portion of a mask of the positive airway pressure system. For example, in some variations, the mask may have an opening to which the airway tubing may be connected. In these variations, the dangling element (104) may be connected to the mask such that it dangles within the opening such as depicted in FIGS. 3A-3C.

Although the FIGS. 3A-3C illustrate the case where the airflow is altered by the dangling element (104) when the user is in a supine position, the dangling element (104) may be configured to instead alter the airflow when in a lateral position instead. This could be achieved with two dangling elements, one on each side of the tube. For example, the airflow tubing (100) may comprise a first dangling element and a second dangling element, each positioned in the channel. The first dangling element may be connected to an inner wall of the airflow tubing (100) on a first side of the airflow tubing (100), and the second dangling element may be connected to an inner wall of the airflow tubing (100) on a second side of the airflow tubing (100) opposite the first side. When the user is in a first lateral position (e.g., on the user's left side), the first dangling element may hang in the airway of the airflow tubing (100) and when the user is in a second lateral position (e.g., on the user's right side), the second dangling element may hang in the airway of the airflow tubing (100). In these variations, each of the first and second dangling elements may include a weight element and a suspension member.

As mentioned above, the positive airway pressure systems may be configured to detect whether a dangling element is hanging in the airway of the airflow tubing, and may be configured to alter the output of a pressure source of the positive airway pressure system based on the detected position of the dangling element (or elements). There are several ways in which the positive airway pressure system may be configured to detect the positioning of the dangling element. In some variations, the dangling element may alter the local pressure in the airway tubing when the dangling element hangs in the airway. One or more air pressure sensors or flow sensors, which may be positioned, for example, in the tubing and/or mask, may detect the change in local pressure, and a portion of the positive airway pressure system (e.g., a controller) may interpret this change to identify the position of the dangling element, and with it, the position of the user (e.g., supine or lateral). In other variations, the dangling element may oscillate when it hangs in the airway. As the dangling element oscillates, it varies the flow of air through the tube, creating an airflow signature that can be interpreted by one or more flow sensors and/or pressure sensors in the system. The one or more flow sensors and/or pressure sensors may be positioned, in the mask, the airway tubing, and/or the console/housing.

Figure 4:
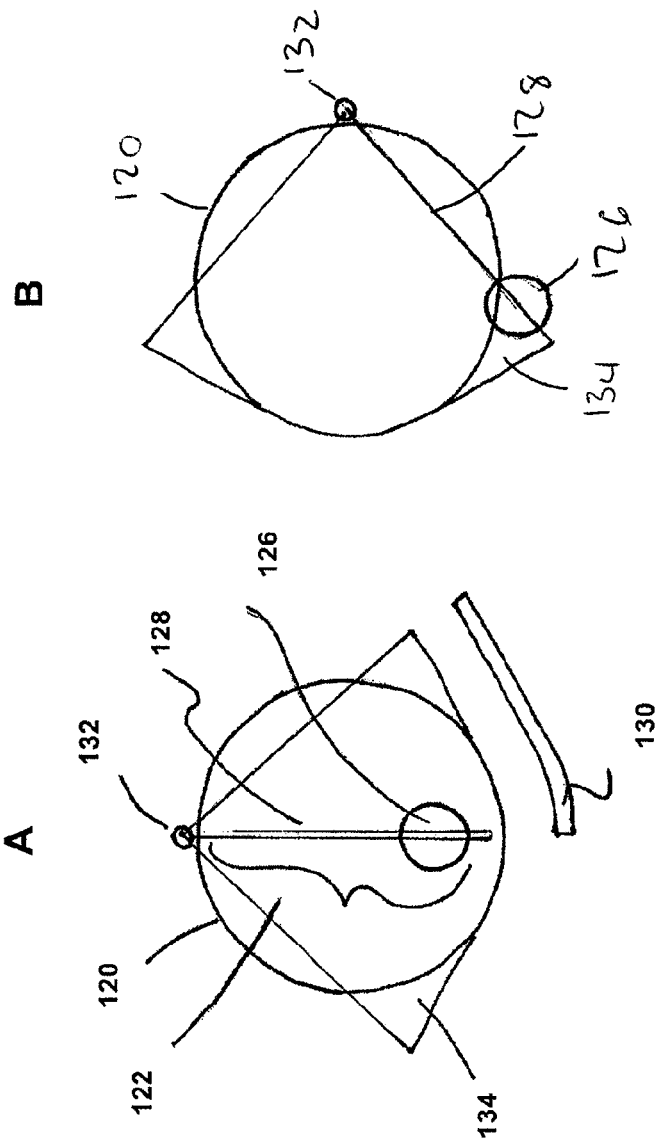
FIGS. 4A and 4B show cross-sectional views of the airway tubing channel with another dangling element to create an air signature to indicate position.

FIGS. 4A and 4B show a diagrammatic cross-sectional view of another embodiment of a dangling element to produce an airflow signature. FIG. 4A shows a cross-sectional view of a segment of airway tubing (120) having a channel (122) therethrough and a dangling element (124) positioned in the channel (122). As shown there, the dangling element (124) may comprise a weight element (126) and a suspension member (128) connecting the weight element (126) to a wall of the airway tubing (120). In some of these variations, the suspension member (128) may be a rod or bar connected to the airway tube (120) at a pivot point (132). The suspension member (128) may be mostly rigid, in that it maintains its shape during rotation of the dangling element (124), such that the weight element (126) is moved in an arc around the pivot point (132) as the dangling element (124) rotates. It should be appreciated that in some instances, the suspension member (128) may slightly flex during oscillation of dangling element (124)

FIG. 4A illustrates the supine position, with gravity (also acting downward from the top of the page, such as discussed above with respect to FIGS. 3A-3C) pulling the dangling element (124) into the air path of the channel (122). When the dangling element (124) hangs in the air path of the channel (122), passing air may cause the dangling element (124) to oscillate, which may alter the pressure and/or air flow through the air path of the channel (122). These pressure oscillations may be sensed by a portion of the positive pressure airway system, and may be used to determine the position of the dangling element, and with it, the user. The pressure oscillations may be sensed by one or more sensors (positioned in the mask, airway tubing, and/or console/housing), such as described in more detail above. When the supine position is detected, the appropriate pressure for the supine position would be administered.

FIG. 4B shows the airway tubing (120) placed in a lateral position, shown rotated 90 degrees clockwise. When the user is in the lateral position, the dangling element (124) may be pulled out of the air path of the channel (122) by gravity. Optionally, the airway tube (120) may comprise a track (130) to guide the dangling element (124) through its range of motion. As mentioned above, the dangling element (124) is suspended from a pivot point (132) which allows it to travel through its full range of motion, which in some instances may include recesses (134) in the air tubing (120) outside of the air path of the channel (122). When in the lateral position, as shown in FIG. 4B, the dangling element (124) may either not alter the airflow passing through the air path of the channel (122), or may alter the pressure and flow differently than when the dangling element (124) is hanging in the supine position. When the dangling element (124) rotates between the lateral and supine positions, the positive airway pressure system may be configured to detect the change in position of the dangling element (124) (which may represent a change in the position of the user), and may alter the output of the pressure source of the system accordingly. For most users, this means a higher PAP pressure when they are sleeping on their backs, and a lower pressure when they are sleeping on their sides. Although the dangling element (124) is shown in FIG. 4B as being positioned in one lateral position, it should be appreciated that in the dangling element (124) may be configured to move from the supine position to either a first lateral position (e.g. on the user's left side) or a second lateral position (e.g., on the user's right side).

Figure 5:
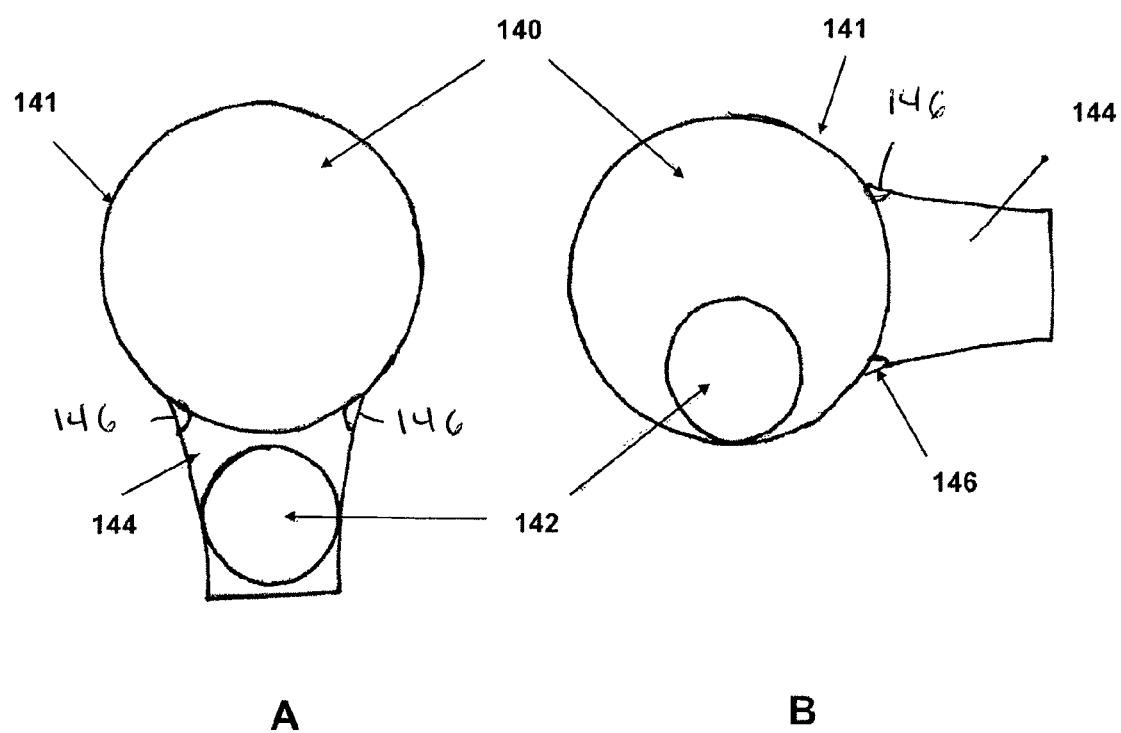
FIGS. 5A and 5B show cross-sectional views of the airway tubing channel with a ball element to create an air signature to indicate position using gravity.

FIGS. 5A and 5B show cross sections of a portion of an airway (140) of a variation of a positive airway pressure system as described here, which may be a bedside or wearable system as described above. While the airway (140) is shown in FIGS. 5A and 5B as being in an air tube (141), the airway (140) may be part of the mask. As shown there, the system may comprise a ball element (142) which may create an air signature when positioned in the airway (140). The ball element (142) is generally a rounded body, and may be of various sizes and/or geometries to affect different air signatures when positioned in the air path (140). The system may further comprise a recess (144) (e.g., in the air tube (141) as shown in FIGS. 5A and 5B, or in a mask), such that the ball element (142) may be moveable into or out of the recess (144) to affect the flow of air through the airway (140)

For example, when a user is in the supine position, illustrated in FIG. 5A, the ball element (142) drops into recess (144) due to gravity. In some variations, the ball element (142) may be entirely housed in the recess (144), such that the ball element (142) does not block the airway (140). In other variations, the ball element (142) may be partially housed in the recess (144), such that only a portion of the ball element (142) impedes the air path.

When the user moves to a lateral position, illustrated in FIG. 5B, the ball (142) rolls out of the recess (144) due to gravity, and into the air path (140). In variations where the ball element (142) is partially housed in the recess (144) when in the supine position, moving to the lateral position may increase the amount of the ball element (142) positioned in the air path (140). As more of the ball element (142) is positioned in the air path (140), the ball element (142) affects the air flow such that an air signature can be perceived by the positive airway pressure system (e.g., via pressure and/or flow sensors in the console/housing, mask, or air tube).

In some variations, tracks or a guide may be added to the air path (140) (e.g., formed on or otherwise attached to an interior wall of the air tube (141) or mask. The tracks or guide may constrain the motion of the ball to ensure the ball's movements stay within a desired path (e.g., the tracks or guides may prevent the ball element (142) from rolling longitudinally along the airway. Additionally or alternatively, the recess (144) may comprise small bumps (146) or a lip at the entrance to the recess (144) to help control when the ball element (142) enters or exits the recess (144). In these variations, the bumps (146) or lip may resist entry of the ball element (142) into the recess (144) and/or resist exiting of the ball element (142) from the recess (144), which may reduce the likelihood that the ball element (142) will not roll in or out do to minor shifts in the user's position.

As mentioned above, in some variations, the ball element (142) may extend at least partially out of the recess in each of the supine and lateral positions, but extend by varying amounts to affect a different air signature in each case. In other variations, the, the ball element may only partially extend out of the recess in one position (e.g., a supine position), and may be fully housed in the side channel in a second position (e.g., a lateral position). For example, in some variations, a flexible suspension element (e.g., a tether, cord, or the like) may limit the amount that the ball element (142) may roll out of the recess (144). As the ball element (142) changes position within the airway (140), the ball element (142) may change the air flow through the airway (140), which may be detected by the system (e.g., via a pressure and/or flow sensor) to detect the positioning of the airway, and the system may be further configured to alter an output of a pressure source of the system based on the detected position.

While the airway (140) is shown in FIGS. 5A and 5B as being configured such that the ball element (142) rolls into the recess (144) in a supine position and outer of the recess (144) in a lateral position, the airway (140) may instead be configured such that the ball element (144) rolls out of the recess (144) in the supine position and into the recess (144) in a lateral position.

In some variations, the positive airway pressure systems described here may be configured and programmed to detect a user's head position based on sound generated in the positive airway pressure system. In these variations, the positive airway pressure system (which may be a wearable or beside system as discussed above) may comprise a sound-generating assembly. The sound-generating assembly may be moveable between a first configuration when a user's head (and thus the mask) is in a first position (e.g., a supine position) and a second configuration when the user's head and mask are in a second position (e.g., a lateral position). The sound-generating assembly may be configured to generate a sound signal in at least one of the first and second configurations, and the system may detect the sound signal generated by the sound-generating assembly (e.g., via a sound sensor such as a microphone) and may alter the output of a pressure source based on the detected sound signal.

For example, in some variations, the sound-generating assembly may generate a first sound signal when the sound-generating assembly is in the first configuration and may generate a second sound signal different than the first sound signal when the sound-generating assembly is in the second configuration. In these variations, the system may be configured to generate a first output with a pressure source when the system detects the first sound signal, and may generate a second output with a pressure source when the system detects the second signal. In other variations, the sound-generating assembly may generate a first sound signal when the sound-generating assembly is in the first configuration and may not generate a sound signal when the sound-generating assembly is in the second configuration. In these variations, the system may be configured to generate a first output with a pressure source when the system detects the first sound signal, and may generate a second output with a pressure source when the system does not detect a sound signal.

In some variations, the sound-generating assembly may be configured to automatically change between the first configuration and the second configuration when the mask is moved between the first and second positions. For example, the sound-generating assembly may include one or more gravity-driven elements that change positions based on gravitational forces to change the sound-generating assembly between first and second configurations as the user and mask move between the first and second positions, respectively.

Figure 6:
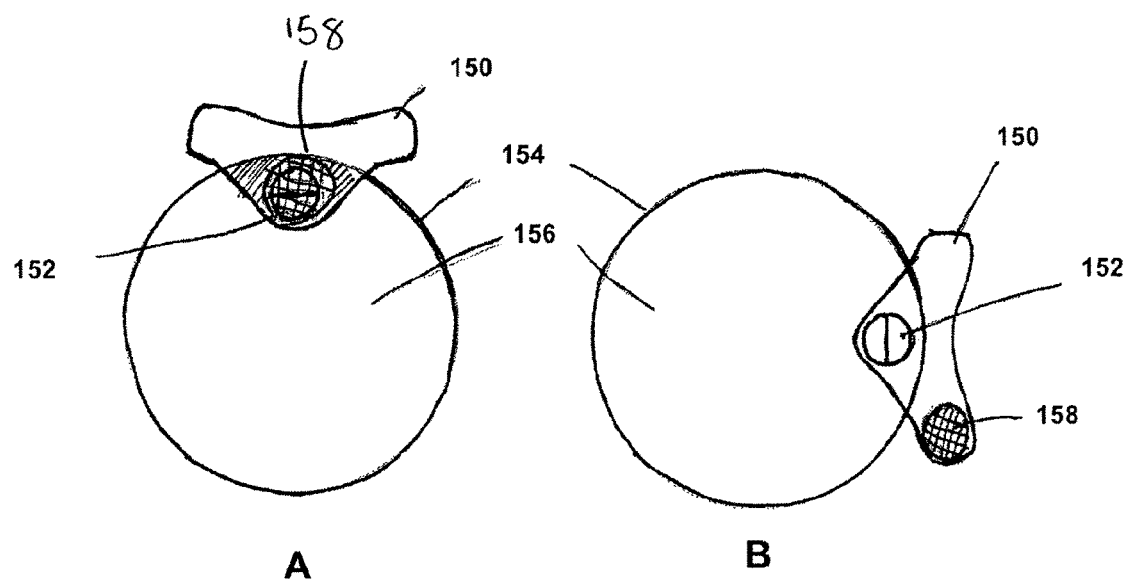
FIGS. 6A and 6B show cross-sectional views of the airway tubing channel with a gravity-driven element to create a sound signature to indicate position.

FIGS. 6A and 6B show cross-sectional views of an airway (156) of a positive airway pressure system as described here, which may be a bedside or a wearable system as discussed above, and which may detect a user's head position using a sound-generating assembly. In the variations shown in FIGS. 6A and 6B, the sound-generating assembly may be positioned in the airway (156) of the air tube (154), although in other variations the sound-generating assembly may be positioned in the airway of the mask.

The sound-generating assembly may comprise a sound-creating element (152) such as a whistle, which may be positioned at least partially in the airway (156) and which generate a sound as air flowing through the airway (156) passes through or around the sound-creating element (152). The sound-generating assembly may further comprise a track (150) at least partially positioned in the airway and having a ball (158) moveable along or within the track (150).

FIG. 6A shows a cross-sectional view of the airway (156) when the user (and the mask) is in a first position (e.g., a supine position), and the sound-generating assembly is in a first configuration. In the first position, gravity may pull the ball (158) to a position in the track (150) that blocks the sound-creating element (152). For example, the track (150) may have a curved shape or a v-shape, and the ball (158) may be pulled to the lowest point in the track (150). In some instances, the ball (158) may entirely block the sound-creating element (152) when the sound-generating assembly is in a first configuration, such that the sound-creating element (152) does not generate a sound signal. In other instances, the ball (158) may partially block the sound-creating element (152), such that the sound-creating element (152) generates a sound signal.

When the user and the mask are rotated to a second position (e.g., a lateral position, which is shown in a cross section in FIG. 6B as rotated 90 degrees clockwise from the first position, but may alternatively be rotated 90 degrees counterclockwise), the sound-generating assembly may change to a second configuration. In some variations, to the ball (158) may roll away from the sound-creating element (152) (e.g., toward the portion of the track (150) that is currently at the lowest point) to move the sound-generating assembly to the second configuration. In some variations, the ball (158) does not block the sound-creating element (152) when the sound-generating assembly is in the second configuration, such that the air may pass around or through the sound-creating element (152) to generate a sound signal. In other variations, the ball (158) may partially block the sound-creating element (152) when the sound-generating assembly, but may still allow for the sound-creating element (152) to generate a sound signal. In variations where the sound-generating assembly generates a first sound signal while in the first configuration, the sound-generating assembly may generate a second sound signal while in the second configuration that is different than the first configuration. In these variations, the system may be configured to detect which sound signal is generated by the sound-creating element to indicate head position of the user, as discussed in more detail above.

While the sound-generating element is shown in FIGS. 6A and 6B as being unblocked to be when the user is in a supine position and unblocked when the user is in a lateral position, the sound-generating assembly may instead be configured such that it is unblocked when the user is in a supine position and is blocked when the user is in a lateral position.

While the sound-generating assembly shown in FIGS. 6A and 6B includes a ball (158) configured to selectively block the sound-creating element, it should be appreciated that the sound-generating assembly may include any suitable blocking member to selectively block the sound-creating element. For example, in some variations the sound-generating assembly may comprise a pivoting disk or plate rotatably connected to a portion of the airway. When in a first configuration, the sound-creating element may be unblocked (completely unblocked or partially unblocked) by the pivoting disk or plate, such that the sound-creating element generates a first sound signal as air flows through the airway. When the mask is rotated (e.g., from a supine to a lateral position, or vice versa), the pivoting disk or plate may rotate to move the sound-generating assembly to a second configuration in which the sound-creating element is at least partially blocked (e.g., either fully blocked such that the sound-creating element does not generate a sound signal, or partially blocked such that the sound-creating element generates a second sound signal different from the first sound signal). The resulting sound signature is information that would be interpreted by the positive airway pressure system (e.g., by the console or housing of the system) to indicate the user's sleeping position, and an output of a pressure source could be adjusted appropriately. Other similar blocking elements may be incorporated into the sound-generating assembly to achieve these results.

Figure 7:
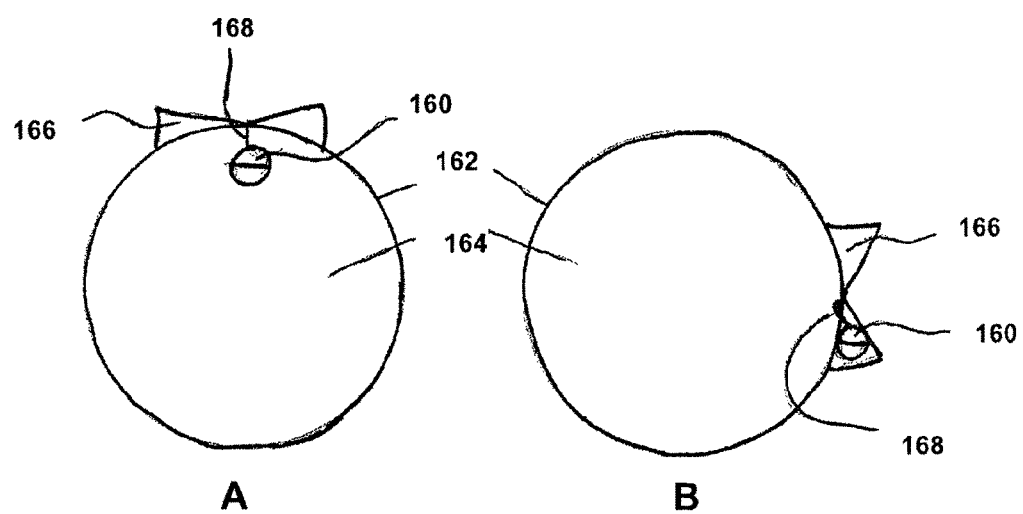
FIGS. 7A and 7B show cross-sectional views of the airway tubing channel with a gravity-driven element to create a sound signature to indicate position.

In other variations, the systems described here may comprise a sound-generating assembly having a sound-creating element configured to move relative to an airway. FIGS. 7A and 7B show cross-sectional views of an airway (164) of a positive airway pressure system as described here, which may be a bedside or a wearable system as discussed above, and which may detect a user's head position using a sound-generating assembly. In the variations shown in FIGS. 7A and 7B, the sound-generating assembly may be positioned in the airway (164) of the air tube (162), although in other variations the sound-generating assembly may be positioned in the airway of the mask.

As shown there, sound-generating assembly may comprise a sound-creating element (160) such as a whistle, which is moveably connected to the airway (164). The sound-generating assembly may be placed in a first configuration when the user and mask are in a first position (e.g., a supine position), in which the sound-creating element (160) is positioned at least partially in the airway (164) such that the sound-creating element generates a first sound signal as air flows through the airway (164). As the user and mask are rotated to a second position (e.g., a lateral position), the sound-generating assembly may automatically move to a second configuration in which the sound-creating element is positioned at least partially out of the airway (164). In some of these variations, the sound-creating element may be positioned entirely out of the airway (164), such that the sound-creating element does not generate a sound signal as air flows through the airway (164). In others of these variations, the sound-creating element may be positioned partially out of the airway (164), but may still generate a second sound signal different than the first sound signal. As air flows through the airway (164). As discussed in more detail below, the system may be configured to detect the sound signals, which may indicate head positioning, and may alter an output of a pressure source based on the same.

The sound-creating element (160) may be connected to the airway in any suitable manner. In the variation shown in FIGS. 7A and 7B, the sound-creating element (160) may be connected to the airway (164) via a suspension member (168), such as those discussed in more detail above. When the user and mask are in a first position (e.g., a supine position), such as shown in FIG. 7A, the sound-generating assembly may be in a first configuration and the sound-creating element (160) may hang in the airway (164), such that passing air actuates the sound-creating element (160) to create a first sound signal (which may be sensed by the positive airway pressure system as discussed above). When the user and mask rotate to a second position (e.g., a lateral position), such as shown in FIG. 7B, the sound-generating assembly may automatically move to a second configuration, and the sound-creating element (160) may be positioned at least partially outside of the airway (164). For example, the air tube (162) or mask may comprise one or more recesses (166) (two recesses are shown in FIGS. 7A and 7B), and gravity may pull the sound-creating element (160) into a recess (166) when in the second configuration. In these variations, the sound-creating element (160) may either not generate a sound signal, or may generate a second sound signal different the first sound signal, such as discussed in more detail above. While shown in FIGS. 7A and 7B as being connected to the airway (164) via a suspension member, it should be appreciated that the sound-creating element may be directly connected to the wall of an air tube, such that the sound-creating element may rotate between the positions described above with respect to FIGS. 7A and 7B. When a sound-creating element is configured to generate one or more sound signals, it may be preferable for the one or more sound signals to be at a frequency or volume that is unperceivable to humans, and in some instances, household pets.

In some variations, the airway of the pressure system may selectively vent air from the airway to the surrounding environment, and may vent different amounts of air depending on the position of the mask and the user. For example, in some variations, the airway may comprise a vent assembly that does not vent any air when the vent assembly is in a first configuration, and vents air when the vent assembly is in a second configuration. For example, the vent assembly may be configured such that it does not vent air when the user is in a supine position, but vents air when the user is a lateral position, which may reduce the pressure of the air supplied to the user when the user in a lateral position. In some of these variations, gravity may move the vent assembly between the first and second configurations (e.g., when the mask and user move between a supine position and a lateral position, or vice versa). In other variations, the vent assembly may vent a first amount of air when the vent is in a first configuration, and may vent a second amount of air different than the first amount when the vent is in the second configuration. For example, the vent assembly may vent a first amount of air when the user is in a supine position, and may vent a larger amount of air when the user is in a later position. Again, gravity may move the vent assembly between first and second configurations as the user changes head positions.

Figure 8:
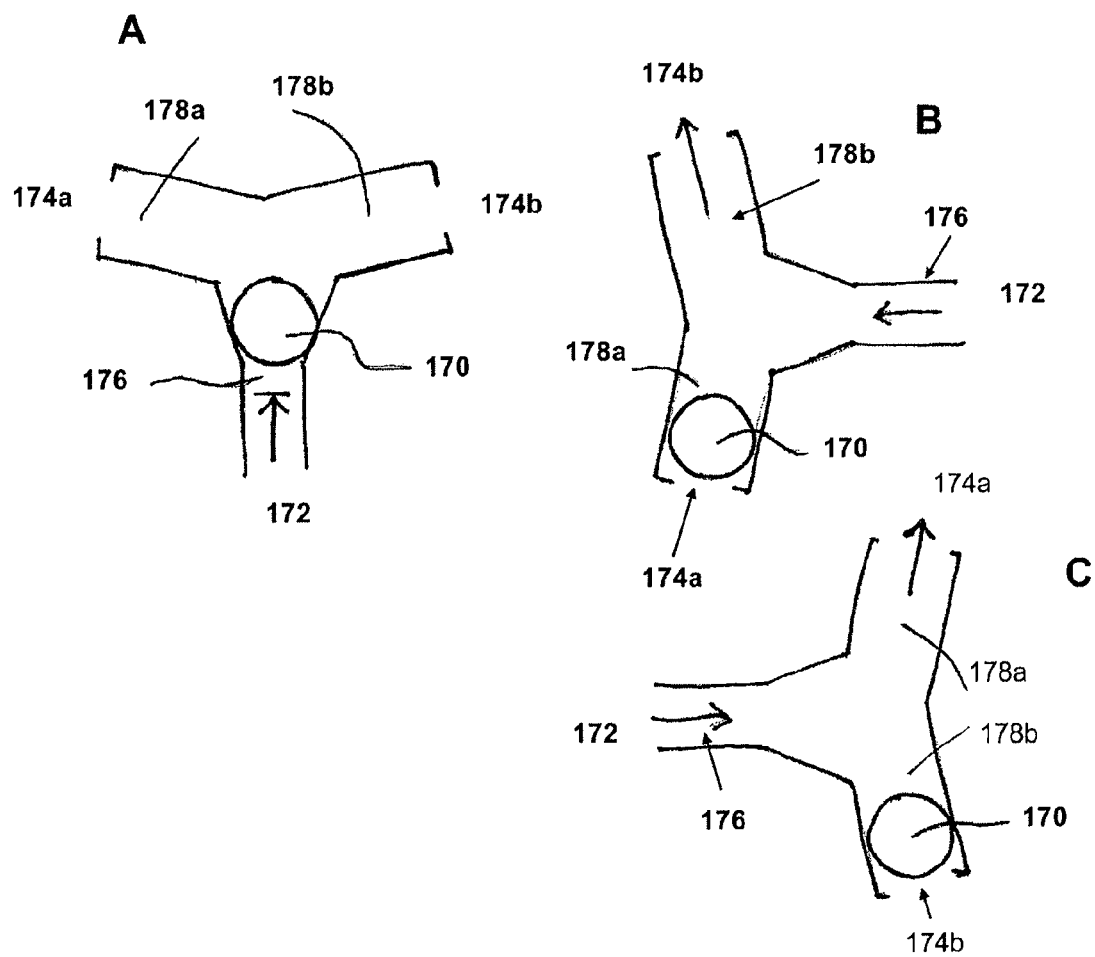
FIGS. 8A-8C show a diagram of a venting system actuated by gravity to lower mask pressure based on position.

FIGS. 8A-8C show a diagram of a vent assembly having ball-valve system that may allow venting of pressure from the airway of a positive airway pressure system when in the lateral position. The vent assembly may be used with any of the wearable or beside positive airway pressure systems as described here. As shown in FIGS. 8A-8C, the vent assembly may have a first channel (176) which may be connected to the airway of the positive airway pressure system to allow air to flow from the airway into the first channel (176). In some variations, the first channel (176) may be connected to the mask (172) of the system, although in other variations the first channel (176) may be connected to an air tube of the system. The first channel (176) may split into first and second side channels, labeled (178a) and (178b) respectively. The vent assembly may further include a first outlet (174a) in the first side channel (178a) and a second outlet (174b) in the second side channel (178b), which may communicate with the interior of the vent assembly and the external environment. The vent assembly may also include a ball (170), which may be configured to selectively control airflow through the vent assembly.

For example, the vent assembly may be configured such that when the user and the mask are in the supine position, as shown in FIG. 8A, gravity pulls the ball (170) into the first channel (176) (which, as mentioned above, may be in communication with the mask (172)), such that the ball (170) may block the first channel (176). When the ball (170) blocks the first channel (176), the ball (170) may block airflow through the channel (176), such that air does not pass through the vent assembly between the airway of the system and the external environment. In these variations, when the user is in the supine position and the ball (170) blocks the channel (176), the mask and user may receive the full pressure generated by the pressure source.

When the user and mask are rotated to a lateral position, the vent assembly may be rotated the ball (170) may roll away from the first channel (176) such that it blocks one of the first or second side channels. For example, when the vent assembly is rotated counterclockwise, as shown in FIG. 8B, the ball (170) may roll to block the first side channel (174a). With the ball (170) blocking the first side channel (174a), air may flow from the airway through the first channel (176) and second side channel (174b), and may exit the vent assembly through the second outlet (174b) in the second side channel (174b). Accordingly, when the vent assembly is in the lateral position, pressure may be vented from the airway to the surrounding atmosphere, which may reduce the pressure supplied to the patient. Similarly, when the vent assembly is rotated clockwise, as shown in FIG. 8C, the ball (170) may roll to block the second side channel (174b), which may allow air to flow through the first channel (176) and the first side channel (174a), and may exit the vent assembly through the first outlet (174a) in the first side channel (174a).

It should be appreciated that the size and geometry of the outlets of the valve assembly may control the rate of the pressure venting, and therefore the pressure drop achieved when the user and mask are in a lateral position. In some variations, one or more outlets may be adjustable. While shown in FIGS. 8A-8C as having two outlets, it should be appreciated that in some variations the vent assembly may have a single outlet. In these variations, the ball may block the outlet when a user and mask are in a supine position, and may leave the outlet open to vent pressure when the user and mask are in a lateral position. For example, in some variations the vent assembly may comprise a semi-spherical chamber. In these variations, the ball may roll to a bottom of the chamber when the user is in a supine position to block an outlet in the bottom of the chamber, and may roll away from the bottom of the chamber when the user is in a lateral position.

Figure 9:
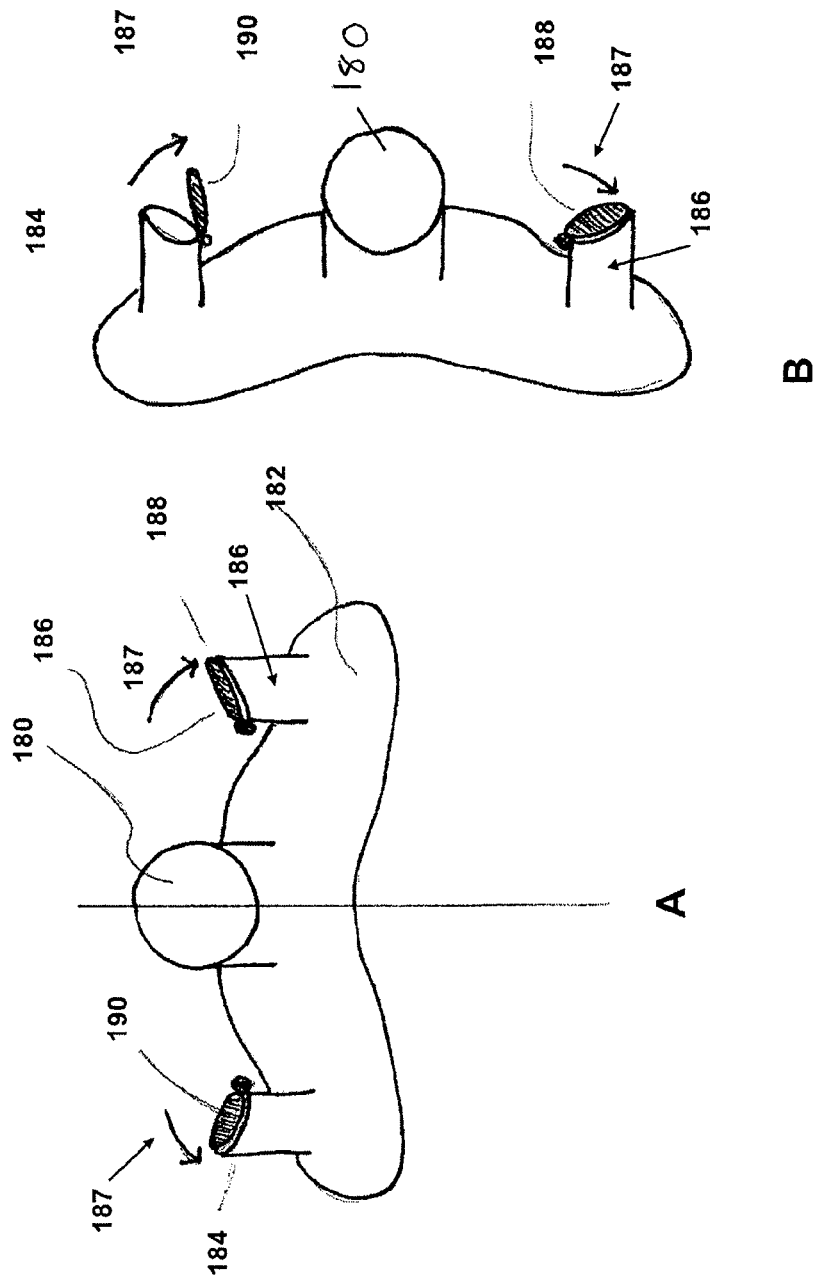
FIGS. 9A and 9B shows a diagram of a valve venting system actuated by gravity to lower mask pressure based on position.

FIGS. 9A and 9B show another variation of a vent assembly as described here. Specifically, the vent assembly may comprise one or more valve ports, each having at least one valve lid. Each valve port may be configured to connect the airway of the system to the external environment, and the valve lid may be opened to allow air to pass from the airway to the external environment and may be closed to block air from passing between the airway and the external environment. In some variations, gravity may move a valve lid between opened and closed configurations. The vent assembly may be used with a wearable or bedside positive airway pressure system, such as discussed in more detail below.

In some variations, the vent assembly may comprise a plurality of valve ports. For example, in the variations shown in FIGS. 9A and 9B, the vent assembly may comprise a first valve port (186) having a first valve lid (188) and a second valve port (184) having a second valve lid (190). While the first and second valve ports are shown in FIGS. 9A and 9B as being connected to the mask (shown partially in FIGS. 9A and 9B as (182)), the valve ports may instead be formed as part of the air tube. FIG. 9A shows the vent assembly in a supine position (e.g., when the mask (182) and user are in a supine position). When the vent assembly is in the supine position, the first (188) and second (190) valve lids may be held closed by gravity against the openings of the respective valve ports (184) and (184) (e.g., arrows (187) depict the direction of travel that gravity may bias or move the valve lids).

When the vent assembly is rotated to a lateral position (e.g., when the mask (182) and user move to a lateral position), one or both of the valve lids may open to allow pressure to vent from the system airway to the external atmosphere. For example, in the variation shown in FIGS. 9A and 9B, when the valve assembly is rotated clockwise, as depicted in FIG. 9B, the valve lid (190) of the second valve port (184) may open (e.g., may be pulled open by gravity) while the valve lid (187) of the first valve port (186) may remain closed. Pressure may be vented through the second valve port (184). Conversely, when the valve assembly is rotated counterclockwise, the valve lid (187) of the first valve port (186) may open while the valve lid (190) of the second valve port (184) may be closed, such that pressure may be vented through the first valve port (188).

While each valve port is shown in FIGS. 9A and 9B as having a single valve lid, each valve port may have multiple lids, which may allow venting through a valve port in either direction. For example, a valve port may comprise a double-hinged valve lid with the ability to open in either direction. When supine, the valve port may remain closed. In one lateral position (e.g., clockwise rotation relative to the supine position), one of the hinged lid segments may open to open the valve and allow venting through the valve port. In the opposite lateral position (e.g., counterclockwise rotation relative to the supine position), the other hinged lid segment would open to open the valve and allow venting through the valve port. Additionally, while shown in FIGS. 9A and 9B as having two valve ports, it should be appreciated that in some instances the vent arrangement may include any number of valve ports. In some variations, the vent arrangement may include only one valve port, which could save space on the system as an advantage.

In still other variations of the devices described here, the system may include a closeable circuit pathway and a circuit-interrupt assembly in operative engagement with the closeable circuit pathway. The circuit-interrupt assembly may be moveable between a first configuration when a mask and user of the system is in a first position (e.g., a supine position) and a second configuration when the mask and user are in a second position (e.g., a lateral position). Specifically, when the circuit-interrupt assembly is in the first configuration, the closeable circuit pathway may form a closed circuit, while when the circuit-interrupt is move to the second configuration, the closeable circuit pathway may form an open circuit. In some variations, gravity may move the circuit-interrupt assembly between the first and second configurations as the mask and user. The system may be configured to determine whether the circuit pathway is currently forming a closed or open circuit, and may alter an output of a pressure source based on the determination. The pathway may be an electrical circuit pathway, and optical circuit pathway, or the like.

Figure 10:
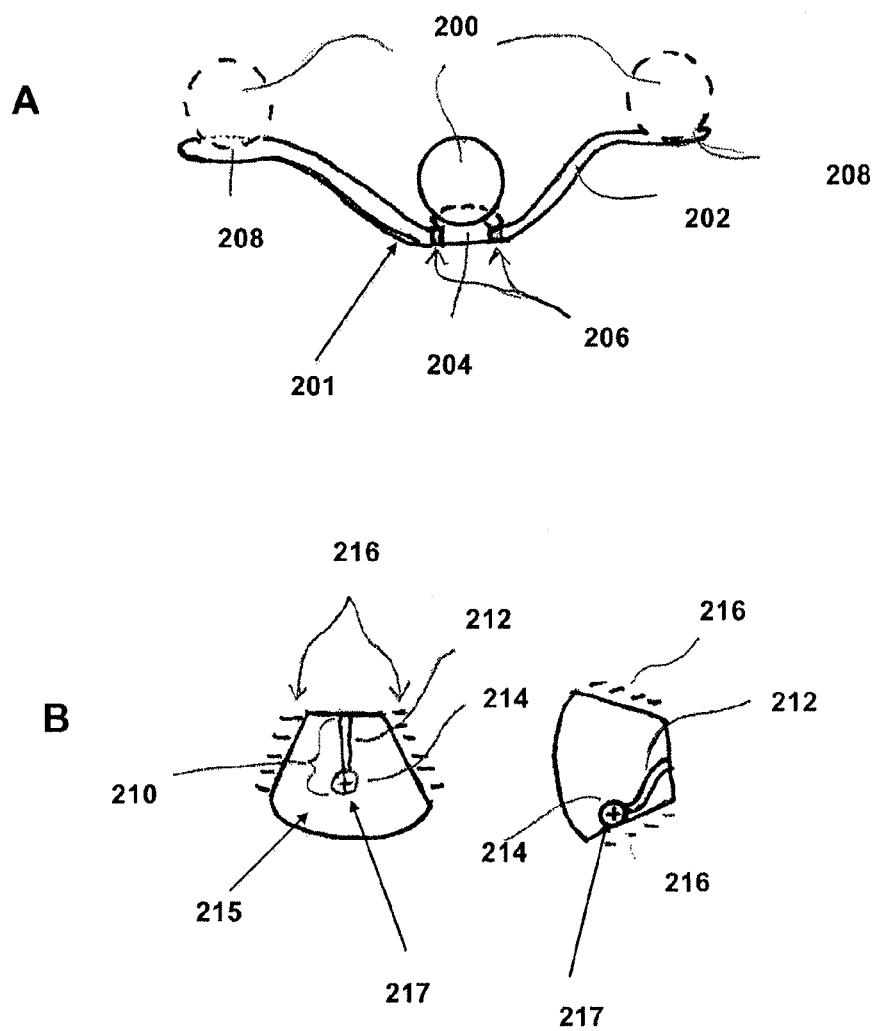
FIGS. 10A and 10B illustrate two mechanisms to produce an electrical signal indicating position based on gravity.

FIGS. 10A and 10B illustrate variations of gravity-driven circuit-interrupt assemblies which may be used to create an electrical signal which can be used to indicate position of the user. FIG. 10A shows one embodiment, in which the circuit-interrupt assembly comprises a ball (200) that is moveable along a track (202). The track (202) may be connected to a portion of the mask or the air tube, and may be at least partially enclosed within a housing (not shown), which may help hold the ball (200) along the track (202). The track (202) may include a lowered mid-section (201) between raised ends (208). The track (202) may be arranged relative to the mask and user such that when the mask and user are in a supine position, gravity pulls the ball (200) toward the lowered mid-section (201). The lowered mid-section (201) that may have two electrical contacts (206), and the ball (200) may contact both of the electrical contacts (206) when positioned in the lowered mid-section (201). The ball (200) may include a conductive outer surface, which may conduct between the first and second contacts (206) to close an electrical circuit. The system (which may be a wearable or bedside system as discussed above) may detect that the electrical circuit is closed, and may generate a first output of a pressure source (e.g., a pressure chosen for supine breathing). In some variations, the track (202) may include a hole (204) or divot between the electrical contacts (206), which may help hold the ball (200) in contact with the electrical contacts (206) when the user and mask are in a supine position.

When the user and mask are rotated to a lateral position, the track (202) may also be rotate such that the ball (200) rolls away from the mid-section (201) to one of the ends (208). This may move the ball (200) out of contact with contacts (206), which may open the electrical circuit. The system may detect that the electrical circuit is open, and may generate a second output of the pressure source (e.g., a pressure chosen for lateral breathing, which may be less than the pressure chosen for supine breathing).

It should be appreciated that the track may be arranged relative the mask such that the ball (200) contacts the contacts (206) to close the circuit when the user is in the lateral position. For example, in some variations, contacts (206) may be positioned in one or more ends of the track (202), such that the ball (200) closes the circuit when the ball rotates to an end of the track. Additionally, while shown in FIG. 10A as opening and closing an electrical circuit, the ball (200) may instead open and close an optical circuit. For example, the ball (200) may be configured to block a light pathway when the track is in a first position (e.g., to open the optical circuit) and may unblock the light pathway when the track is in a second position (e.g., to close the optical circuit).

FIG. 10B shows a second gravity-driven circuit-interrupt assembly. As shown there, the circuit-interrupt assembly may comprise a chamber (215) having conductive plates (216). The circuit-interrupt assembly may further comprise a dangling element (217) connected to the chamber (215). The dangling element (217) may comprise a weighted element (214) (such as those described in more detail above) with a conductive surface suspended by a suspension member (212), which may be any suitable suspension member such as described in more detail above. The stiffness of the suspension member (212) can be adjusted to accomplish the desired sensitivity to positional movement and may include one or more polymer, elastomer, paper, fiber or other materials with the desired properties. The suspension member (217) and the conductive plates (216) may be part of a closeable electric circuit. In the supine position, the dangling element (217) may hang between two conductive plates (216), such that there is no contact between the dangling element (217) and the conducting elements of the walls (216). In these instances, the loop is open. When the circuit-interrupt assembly is moved to either lateral position, gravity may pull the weighted element (214) dangling element (217) into contact with one of the side plates (216), which closing the loop of the closeable circuit. The system may be configured to detect whether the circuit is opened or closed, and may alter an output of a pressure source based on whether the circuit is opened or closed. In some varia-tions, the functional states of the switch could be reversed such that the circuit is open when the user is in the lateral position and the circuit is closed when the user is supine. Further, the circuit-interrupt assembly of FIG. 10B may be used with a closeable optical circuit (e.g., the dangling element may block an optical pathway in one position, such as the supine position, and may unblock the optical pathway in a second position, such as the lateral position).

In many cases it may be desirable to determine the patient's position using an accelerometer or similar position sensor, which may be connected to a portion of a mask or air tube of a positive airway pressure system as described here. Although the cost of electronics tends to continue to decline as volumes increase, many of these sensors may be too expensive to be disposed every three months with the masks and air tubes. Thus, in many cases it would be advantageous to have a reusable sensor element that can be removed from a mask prior to its disposal, and then securely fastened to a new replacement mask. The challenge that such a use pattern brings is how to reliably place the sensing element onto the replacement mask. In many instances, the sensing element may need to remain fixed in place, and (especially in the case of an accelerometer) it may need to be specifically oriented or calibrated in order to accurately provide accurate position information. Accordingly, it may be desirable to allow repeatable connection of a reusable sensor to a mask or air tube with a known orientation relative to the mask or air tube.

Accordingly, some of the positive airway pressure systems described here may comprise a reusable position sensor that may be releasably connected to a portion of the system. In some variations, the reusable position sensor may be releasably connected to a mask of the system. In other variations, the reusable position sensor may be releasably connected to an air tube. The reusable position sensor, which may be an accelerometer, may also be configured to communicate (e.g., wireless, via temporary wired connection) head position information to a portion of the system (e.g., a controller, microprocessor, or other control circuitry, e.g., in the wearable housing or a bedside unit). The system may be configured to alter an output of a pressure source based on the head position information, such as described above.

In some instances, the position sensor may be part of a position sensor assembly may require a predetermined orientation relative to the mask or the air tube during attachment of the position sensor assembly to the mask or air tube. If the position sensor assembly is attached to the same spot with the same orientation on different masks, it may not be necessary to recalibrate the position sensor when the use replaces mask and air tubes. In some instances, the position sensor assembly may be keyed to require a specific orientation between the position sensor assembly and the mask or air tube of the positive airway pressure system.

FIGS. 11A and 11B show ways to produce keyed position sensor assemblies that can be detached and reattached in a repeatable orientation. For example, FIG. 11A shows a geometry keying system. As shown there, the positive airway pressure system may comprise a base (1100) and a position sensor assembly (1102). The base (1100) may be attached to or otherwise formed as part of the mask or air tube assemblies. The position sensor assembly (1102) may have a housing (1104) which may be connected to the base (1100). In some variations, such as shown in FIG. 11A, the base (1100) may have a recess (1106) into which a portion of the housing (1104) may fit. Generally the recess (1106) and the housing (1104) may be sized and shaped to require a specific orientation between the position sensor assembly (1102) and base (1100).

For example, in the variation shown in FIG. 11A, the recess (1106) may comprise a circular shape having a triangular extension. Similarly the housing (1104) may have a circular shape having a triangular extension. To connect the position sensor assembly (1102) to the base (1100), the housing (1104) may be oriented to align the triangular extension of the housing (1104) with the triangular extension of the recess (1106), which may provide a specific alignment between position sensor assembly (1102) and the base (1100).

While the housing (1104) is shown in FIG. 11A as being sized to fit entirely within the recess (1106), it should be appreciated that the housing may (1104) may instead comprise a projection (not shown) sized and shaped to be aligned with and fit within the recess (1106). In other variations, the base (1100) may comprise a projection and the housing (1104) of the position sensor assembly (1102) may comprise a recess to receive the projection, wherein the projection and recess are sized and shaped to require a specific orientation between the base (1100) and the position sensor assembly (1102).

While the shapes described above include a circular shape with a triangular extension, it should be appreciated that the base (1100) and position sensor assembly (1102) may have any geometries to require a particular orientation between the base (1100) and the position sensor assembly (1102). In some variations, the keyed geometries may be configured such that the base (1100) and position sensor assembly may have a single possible orientation when the base and position sensor assembly are connected. In other variations, the keyed geometries may allow for two possible orientations (e.g., which may in some instances be 180 degrees apart from each other). For example, the recess may be rectangular in shape, and the housing may have a correspondingly rectangular shape, such the housing may be connected to the base in one of two different orientations.

Additionally or alternatively, the base and the position sensor assembly may be configured to magnetically align. For example, FIG. 11B shows a different method for keying the sensor attachment using magnets. As shown there, the system may comprise a base (1108) and a position sensor assembly (1110). Each of the base (1108) and position sensor assembly (1110) may include at least one magnet (1112) imbedded therein or otherwise attached thereto. For example, the base (1108) and position sensor assembly (1110) is shown in FIG. 11B as each having two magnets (1112). When the position sensor assembly (1110) is brought near the base (1108), the magnets (1112) of the position sensor assembly (1110) may attract the magnets (1112) of the base (1108), which may hold position sensor assembly (1110) against the base (1108). Further, the attraction of the magnets (1112) may align the position sensor assembly (1110) relative to the base (1108). In some instances, the magnets (1112) may resist attachment when the position sensor assembly (1110) and the base (1108) are not aligned. It should be appreciated that the position sensor assembly and base may also be geometrically keyed as discuss above.

The base (1108) may be part of a mask or an air tube, such as discussed above. In some variations, base (1108) could be snapped into place on the mask or molded into place on the mask during manufacturing. Alternatively, the base (1108) may be removable attached to a mask, such that both the base (1108) and the position sensor assembly may removable and reusable. For example, the base and the position sensor assembly may be placed on opposite sides of a portion mask material (e.g., a strap) such that when they are magnetically coupled, they capture an amount of mask material between them.

Another way to indicate the position of the sleeper is through the use of pressure and/or contact sensors. Pressure sensors may measure the force applied to them, while contact sensors determine whether or not there is sufficient force on to indicate contact of an object with the contact sensor. Either type of sensor could be used to indicate the position of a sleeper (e.g., by measuring contact or force between the sensor and a sleeping surface such as a bed or pillow), and the term "force sensor" will be used here to interchangeably refer to a contact or pressure sensor. On a positive airway pressure system as described here, there are many potential locations for the placement of force sensors. For example, to determine whether the sleeper is in the supine or lateral positions, force sensors may be placed on the sides and the back of the head. When the forces sensors detect pressure or contact on the back of the head, the user is likely to be in a supine position. Similarly, when the force sensors detect pressure or contact either side of the head, the user is likely to be in a lateral position.

Figure 12:
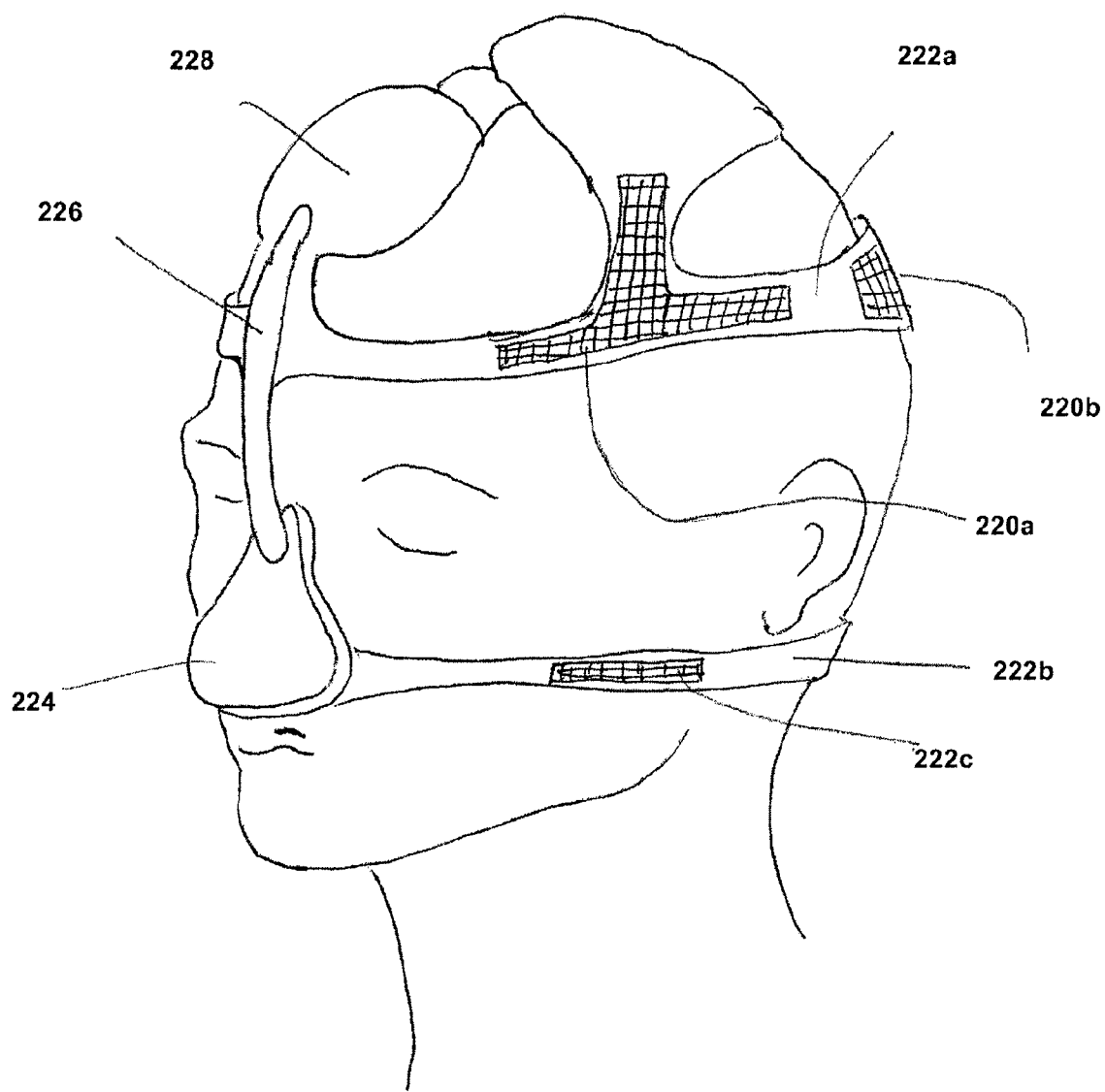
FIG. 12 shows potential placement areas for force sensors on a system.

When the systems described here comprise force sensors (e.g., pressure and/or contact sensors), these sensors can be placed on the straps, scaffolding, device, tubing, fasteners, or any other part of the positive airway pressure system which is mounted on the user's head. FIG. 12 shows some potential placement zones for force sensors on a wearable positive airway pressure system having a mask (224), an air tube (226), and a wearable housing (228), such as discussed in more detail above. Additionally shown there are first and second straps (222a) and (222b) configured to connect the wearable housing (228) and the mask (224), respectively, to a user.

The force sensors are most useful when placed in two general areas: the back of the head and the sides of the head. The sensors placed on the back of the head indicate when the user is in the supine position, while the sensors placed on the sides of the head indicate when the user is in either lateral position. For example, in the variation shown in FIG. 12, the system may comprise a first side force sensor (220a) positioned on the strap (222a) on a first side of the user's head, a second side force sensor (not shown) on the strap (222a) an opposite side of the user's head, and a rear force sensor (220b) on the strap (220a) on the back of the user's head. Additionally, the strap (222b) may comprise one or more side force sensors and/or a rear force sensor (only a first side sensor (220c) on the strap (222b) is shown). When the system is worn by the user, the rear force sensors (e.g., rear sensor (220b)) may be positioned along a back of the user's head while the side force sensors (e.g., side force sensor (220a) and (220c)) along the sides of the user's heard. The side and rear force sensors may be used to determine head position, such as described in more detail below. The sensor placement zones are just for purposes of example, and not limiting as to where the force sensors could be placed. Additionally, while the system shown in FIG. 12 is wearable, it should be appreciate that a bedside system may include side and/or rear force sensors (e.g., which may be attached to one or more straps or portions of a mask).

Further, while shown in FIG. 12 as having both rear and side force sensors, the system may include only side force sensors or only rear force sensors. For example, to save complexity, space and cost, a force sensor or force sensors could be placed only on the back of the head. In these variations, when the rear force sensors detect contact/pressure, the positive airway pressure system may determine that the user is in a supine position, and may generate a first output from a pressure source of the system (e.g., a pressure selected for supine position breathing). When the rear force sensors do not detect contact/pressure, the positive airway pressure system may place the system in a lateral setting, and may generate a second output from a pressure source of the system (e.g., a pressure selected for lateral position breathing, which may be a lower pressure than the first output). In other variations, the force sensors could be placed only on the sides of the head. In such a case, the positive airway pressure system may generate a first output of a pressure source when none of the force sensors detect contact or pressure (e.g., a pressure selected for supine position breathing), and may generate a second output of the pressure source when one or more of the force sensors detect contact or pressure (e.g., a pressure selected for lateral position breathing, which may be a lower pressure than the first output).

The force sensors described above may be disposable or reusable. In some variations, the force sensors may be incorporated into a reusable sensor assembly that may be geometrically and/or magnetically keyed with a portion of the system (e.g., a mask, strap, or the like) to set a specific orientation between the force sensor and the rest of the positive airway pressure system. When a force sensor is reusable, the sensors may be removed and replaced on a new set of headgear, mask, straps, scaffold, etc. Alternatively, the sensors could be attached to a part of the PAP system that is already intended to be reused (e.g., the wearable housing of a wearable system as described above).

Figure 13:
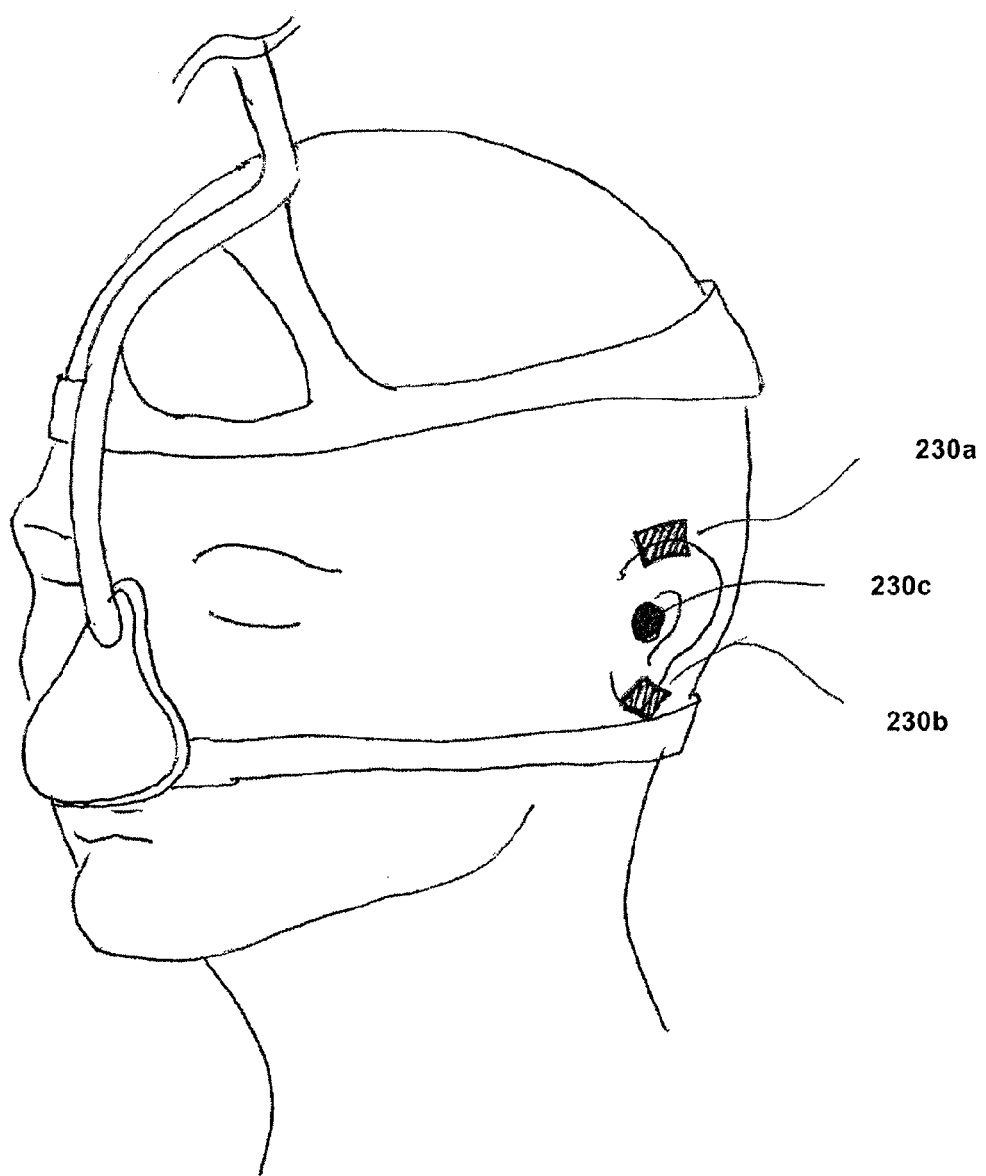
FIG. 13 shows potential placement areas for force sensors on the ear.

In other variations, a force sensor may be configured to be connected directly to a portion of a user (as opposed to being connected to a portion of the positive airway pressure system worn by the user). In some variations, one or more force sensors may be connected to an ear of the user. The ear provides a natural placement for such sensors—since they would be in contact with bedding when the user is in the lateral position. For example, FIG. 13 shows potential sensor mounting areas on the ear. As shown there, a first force sensor (230a) may be connected to a top of the ear, a second force sensor (230b) may be connected to the lobe of the ear, and a third force sensor (230c) which may be at least partially positioned in the ear canal. While all three sensors are shown in FIG. 13, the system may include any number of sensors attached to the ear in any of the above locations. Additionally, while only one of the ears are shown in FIG. 13, it should be appreciated that at least one force sensor may be releasably connected to each ear of a user.

The force sensors may be connected to a user in any suitable manner. In some variations, a force sensor may be incorporated into a clip which may be clipped to a portion of the ear (e.g., the top of the ear and/or the lobe of the ear). In other variations, the force sensor may be incorporated into an ear plug, which may be inserted into the ear canal. The ear canal further provides the opportunity for the sensor to be combined with a noise-dampening material to aid sleep by blocking out noise from the surrounding environment, including the PAP device. The ear lobe and external ear structures are good attachment surfaces as they do not have many nerves, and thus a secure attachment can be made without discomfort to the user. In other variations, one or more force sensors may be connected to a user via an adhesive patch.

Figure 14:
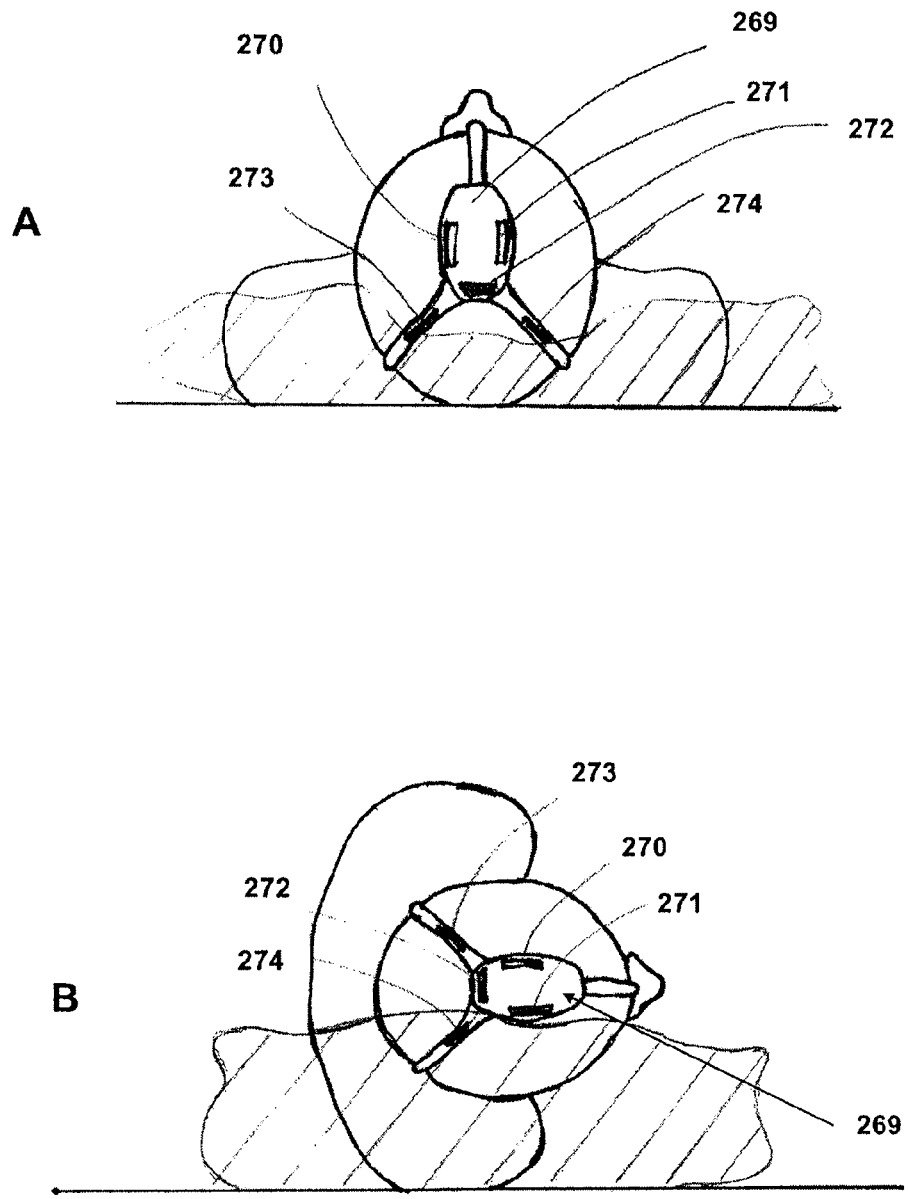
FIGS. 14A and 14B show potential placement areas for force sensors on a system in both the supine and lateral positions.

FIGS. 14A and 14B show one manner in which force sensors may be used by a positive airway pressure system to determine whether a user is in the supine or lateral sleeping positions. While shown as a wearable system (e.g., having a wearable housing (269)), it should be appreciated that the system may be a bedside system. As shown there, the system may comprise three rear force sensors (272), (273), and (274). One force sensor (272) may be connected to a wearable housing (269), and two of the rear force sensors (273) and (274) may be connected to straps on either side of the force sensor (272) connected to the wearable housing (269). Additionally, the system may include first and second side sensors (270) and (271) (the first side sensor (270) may be on the same side of the user as the rear force sensor (273) while the second side sensor (271) may be on the same side of the user as the rear force sensor (274)). While the first and second side sensors (270) and (271) are shown in FIGS. 14A and 14B as being connected to the wearable housing (269), the first and second side sensors (270) and (271) may be attached to straps, or may be connected directly to the user, such as discussed above.

In FIG. 14A, the user is in the supine position and the rear force sensors located on the back of the wearable housing (272) and the rear straps (273 and 274) may be in contact with the bedding material, and the rear force sensors may detect this contact and communicate this information to the system. The system may then generate a first output with a pressure source of the system (e.g., a pressure that may be selected for supine breathing). When a user moves to a lateral position, as shown in FIG. 14B, one of the side sensors (e.g., the side sensors (271) on one side of the wearable housing (269) and same side as for the force sensor (274) on the rear strap) is moved into contact with the bedding material, thereby indicating the lateral position to the device. When a side force sensor indicates contact (and/or when rear force sensor ceases indicating contact), the system may generate a second output with a pressure source of the system (e.g., a pressure selected for lateral breathing, which may be less than the pressure selected for supine breathing).

In some variations, the system may include one or more proximity sensors configured to determine the sleeping position of a user. For example, FIGS. 15A and 15B show how proximity sensors could be used to indicate sleeping position. As shown there, the system may comprise a first proximity sensor (240), a second proximity sensor (242), and a sensing base (254). The system may be configured to measure the distance between the first proximity sensor (240) and the sensing base (254) and the distance between the second proximity sensor (242) and the sensing base (254). These distances may be used to determine a user's head position. The proximity sensors may be connected to any suitable portion of the patient (e.g., connected to a wearable housing in a wearable system, to a portion of a mask, one or more straps, or the like). The sensing base (254) may be placed on or under a sleeping surface (244) on which the user sleeps (e.g., the sensing base may be placed on or under a mattress pad, within a pillow, or the like). The sensing base (254) may be flexible or rigid, and may be powered by wall outlet, one or more batteries, or a combination thereof.

In the variation shown in FIGS. 15A and 15B, the first proximity sensor (240) may be positioned closer to a user's face while the second proximity sensor (242) may be positioned closer to the rear of the user's head. When the user's head is within a range (252) from the supine position (e.g., about thirty degrees on either side of supine position), as shown in FIG. 15A, the first and second proximity sensors may each have a relatively controlled distance from the sensing base (254). For example, the distance between first proximity sensor (240) and the sensing base (254) may be in a first range of distances (shown in FIG. 15A as between distances (248) and (250)), while the second proximity sensor (240) and the sensing base (254) may be in a second range of distances (shown in FIG. 15A as distance (246)) which is less than the first range of distances. Accordingly, the system may be configured to calculate the difference between the distance between the first proximity sensor (240) and the sensing base (254) and the distance between the second proximity sensor (242) and the sensing base (254). If this difference is larger than a threshold value, the system may determine that the user must be in the supine position, and can adjust the output pressure accordingly.

FIG. 15B shows the user in the lateral sleeping position. Here, first and second proximity sensors may each be about the same distance from the sensing base (254). For example, as shown there, both the first proximity sensor (240) and the second proximity sensor (242) may remain within a distance band (256) between distances (258) and (260), even if the user shifts slightly within a lateral position. When the difference between the distance between the first proximity sensor (240) and the sensing base (254) and the distance between the second proximity sensor (242) and the sensing base (254) is below a threshold value, the system may determines that the user is in the lateral position.

It is possible to achieve a similar system with only one proximity sensor mounted on the user. However, since there is considerable variability in the thickness of the bedding material used by different sleepers, utilizing two or more proximity sensor may allows for greater certainty of determining the sleeping position accurately independent of bedding materials. Additionally, in some variations one or more of the proximity sensors may be releasably attached to the system (e.g., a portion of a mask, air tubing, wearable housing).

While particular forms of the devices and methods described here have been illustrated and described herein, it will be apparent that various modifications and improvements can be made to the devices and methods. For example, while the description herein has focused on PAP systems, the system may be utilized in a variety of breathing systems. Additionally, the PAP systems are primarily described herein as self-contained breathing systems. However, many of the advantageous features described herein may be applicable to breathing systems with remote control and/or pressure sources and wherein the head position sensor is secured to the top of the patient's head. To the extent not otherwise described herein, materials and structure may be of conventional design.

Moreover, individual features of embodiments of the devices and methods may be shown in some drawings and not in others, but those skilled in the art will recognize that individual features of one embodiment of the devices and methods can be combined with any or all the features of another embodiment. Accordingly, it is not intended that the devices and methods be limited to the specific embodiments illustrated. As used here, "about" means±5%.

What is claimed is:

1. A positive airway pressure system comprising:
    a wearable mask for delivery of pressurized air to a user;
    a pressure source configured to provide the pressurized air;
    an airway tube connecting the mask and the pressure source, the airway tube and mask defining an airway between the pressure source and the user;
    an airflow-altering element positioned at least partially in the airway, the airflow-altering element moveable between a first position when the mask is in a first position and a second position when the mask is in a second position and wherein the airflow-altering element is configured to alter flow of the pressurized air in the airway in at least one of the first and second positions; and
    at least one sensor configured to detect alterations in the flow of the pressurized air,
    wherein the system is configured to alter an output of the pressure source based on a position of the airflow-altering element using an output of the at least one sensor.

2. The system of claim 1 wherein gravity moves the airflow-altering element between the first and second positions.

3. The system of claim 1 wherein the first position of the mask corresponds to a supine head position when the mask is worn by the user.

4. The system of claim 3 wherein the second position of the mask corresponds to a lateral head position when the mask is worn by the user.

5. The system of claim 1 wherein the airflow-altering element comprises a weight member and a suspension member connecting the weight member to a wall of the airway tube.

6. The system of claim 5 wherein the weight member is configured to hang from the wall of the airway tube when the airflow-altering element is in the first position.

7. The system of claim 6 wherein the airway comprises at least one recess, and wherein the weight member is configured to rest at least partially in the recess when the airflow-altering element is in the second position.

8. The system of claim 6 wherein the airflow-altering element in the first position is configured to oscillate during flow of the pressurized air past the airflow-altering element.

9. The system of claim 1 further comprising a controller, wherein the controller is configured to receive the output of the at least one sensor and set the output pressure based on the output of the at least one sensor.

10. A mask assembly for use with a positive airway pressure system comprising:
    a wearable mask for delivery of pressurized air to a user;
    an airway tube for connecting the mask to a pressure source, the airway tube and mask defining an airway therethrough;
    an airflow-altering element positioned at least partially in the airway, the airflow-altering element moveable between a first position when the mask is in a first position when worn by the user and a second position when the mask is in a second position when worn by the user, wherein a position of the airflow-altering element is dependent upon a position of the mask, and wherein the airflow-altering element is configured to alter flow of the pressurized air in the airway in at least one of the first and second positions.

11. The assembly of claim 10 wherein gravity moves the airflow-altering element between the first and second positions.

12. The assembly of claim 10 wherein the first position of the mask corresponds to a supine head position.

13. The assembly of claim 12 wherein the second position of the mask corresponds to a lateral head position.

14. The assembly of claim 10 wherein the airflow-altering element comprises a weight member and a suspension member connecting the weight member to the airway.

15. A method for providing pressurized air to a user's airway comprising:

delivering pressurized air to the user using an air pressure system comprising:
a wearable mask for delivery of the pressurized air to the user,
a pressure source configured to provide the pressurized air,
an airway tube connecting the mask and the pressure source wherein the airway tube and mask defining an airway between the pressure source and the user, and
an airflow-altering element positioned at least partially in the airway, wherein the airflow-altering element is moveable between a first position when the mask is in a first position and a second position when the mask is in a second position and wherein the airflow-altering element is configured to alter flow of the pressurized air in the airway in at least one of the first and second positions;
monitoring the flow of pressurized air through the airway to determine a head position based on a position of the airflow-altering element; and
altering an output of the pressure source based on the determined head position.

16. The method of claim 15 wherein gravity moves the airflow-altering element between the first and second positions.

17. The method of claim 15 wherein the first position of the mask corresponds to a supine head position when the mask is worn by the user.

18. The method of claim 17 wherein the second position of the mask corresponds to a lateral head position when the mask is worn by the user.

19. The method of claim 15 wherein the airflow-altering element in the first position is configured to oscillate during flow of the pressurized air past the airflow-altering element.

20. The method of claim 15, wherein monitoring the flow of pressurized air comprises detecting oscillations of the airflow-altering element.

* * * * *